United States Patent [19]

Nakahara et al.

[11] Patent Number: 4,481,317
[45] Date of Patent: Nov. 6, 1984

[54] HINDERED BISPHENOL DIPHOSPHONITES AND STABILIZED SYNTHETIC RESIN COMPOSITIONS CONTAINING THE SAME

[75] Inventors: Yutaka Nakahara, Iwatsuki; Tohru Haruna, Okegawa; Etsuo Tobita, Tokyo, all of Japan

[73] Assignee: Adeka Argus Chemical Co., Ltd., Urawa, Japan

[21] Appl. No.: 501,946

[22] Filed: Jun. 7, 1983

[51] Int. Cl.³ .......................... C08K 5/53; C07F 9/02
[52] U.S. Cl. ................. 524/119; 260/927 R; 260/936
[58] Field of Search ............... 524/117, 119, 120, 121, 524/128, 135, 342; 260/927 R, 936

[56] References Cited

U.S. PATENT DOCUMENTS

| | | | |
|---|---|---|---|
| 3,234,285 | 2/1966 | Moss et al. | 524/343 |
| 3,429,837 | 2/1969 | Langrish et al. | 524/333 |
| 4,107,138 | 8/1978 | Hofer et al. | 524/135 |
| 4,143,028 | 3/1979 | Spivack | 524/117 |
| 4,348,495 | 9/1982 | Buysch et al. | 524/119 |

Primary Examiner—John Kight
Assistant Examiner—Kriellion Morgan

[57] ABSTRACT

Hindered bisphenol diphosphonites are provided having the structure:

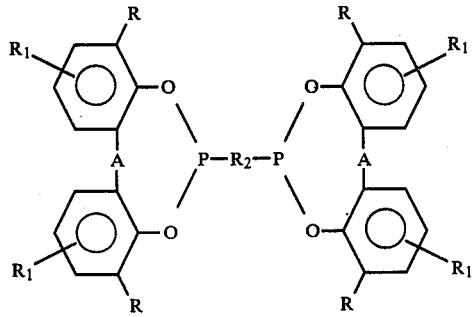

wherein:

A is selected from the group consisting of thio sulfur —S—; oxy oxygen —O—; alkylidene having from one to about ten carbon atoms; cycloalkylidene having from about four to about eight carbon atoms; and phenylalkylidene having from seven to about twelve carbon atoms;

R is selected from the group consisting of alkyl having from one to about eighteen carbon atoms; cycloalkyl having from three to about twelve carbon atoms; and aralkyl having from seven to about twelve carbon atoms;

$R_1$ is selected from the group consisting of hydrogen; alkyl having from one to about eighteen carbon atoms; cycloalkyl having from three to about twelve carbon atoms; and aralkyl having from seven to about twelve carbon atoms;

$R_2$ is selected from the group consisting of

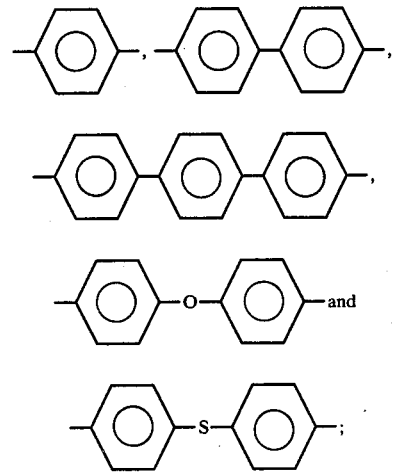

as well as synthetic resin compositions having an enhanced resistance to deterioration by heat and light comprising a synthetic resin and such phosphonites.

38 Claims, No Drawings

HINDERED BISPHENOL DIPHOSPHONITES AND STABILIZED SYNTHETIC RESIN COMPOSITIONS CONTAINING THE SAME

Synthetic resins such as polyethylene, polypropylene, polystyrene and polyvinyl chloride show a strong tendency to deteriorate in physical properties at elevated temperatures and when exposed to ultraviolet light. The deterioration is evidenced by, among other things, a decrease in viscosity, a tendency to become brittle, and discoloration. This deterioration can be accompanied by distortion, cracking, and powdering of the material. To overcome these difficulties, many stabilizers have been proposed for combination with synthetic resins, among them, organic phosphonites.

Bown and McDougall U.S. Pat. No. 3,297,631, patented Jan. 10, 1967, provides condensation products of phosphorus compounds with bisphenols and trisphenols which are stabilizers, especially for polyolefins, and which may be represented by the structures:

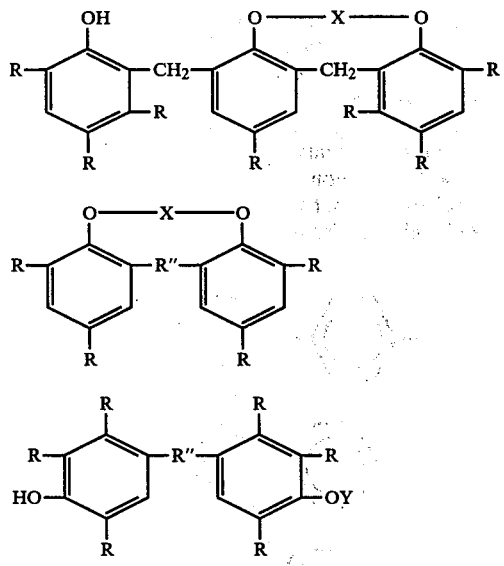

Where:
X is selected from the following: $>$P—OR'; $>$P—R';

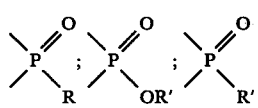

and
Y is selected from the following: —P(OR')$_2$;

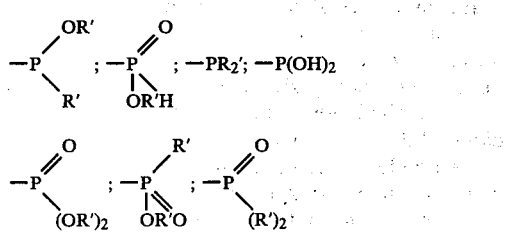

R is hydrogen, an alkyl group having 1 to 16 carbon atoms, or an aryl group, or a combination thereof;
R' is an alkyl group having 1 to 16 carbon atoms or an aryl group; and
R" is an alkylidene having 1 to 16 carbon atoms or an aryl-substituted alkylidene.

Spivack U.S. Pat. No. 4,143,028, patented Mar. 6, 1979, provides alkylated 1,1'-biphenyl-2,2'-diyl phosphonites prepared by reacting alkylated 2,2'-dihydroxybiphenylene with dichloroaryl or dichloroalkyl phosphine in an organic solvent, and useful as stabilizers of organic polymers and lubricating oils, especially as process stabilizers for polyolefins, represented by the formula

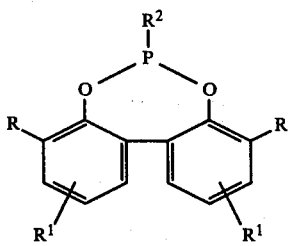

wherein
R is an alkyl group of 1 to 18 carbon atoms,
R$^1$ is hydrogen or an alkyl group of 1 to 18 carbon atoms, and
R$^2$ is an alkyl group of 1 to 18 carbon atoms, phenyl, phenyl substituted with up to 3 alkyl groups each having 1 to 8 carbon atoms, or a group of the formulae

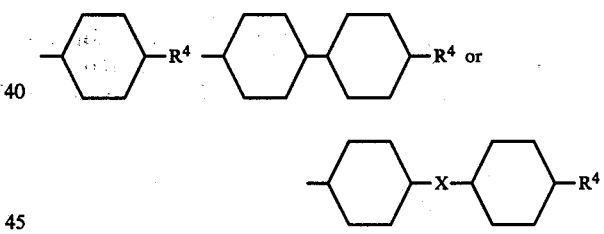

where
R$^4$ is of the formula

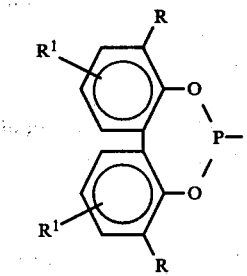

and
X is O or S.

Hofer and Tscheulin U.S. Pat. No. 4,075,163, patented Feb. 21, 1978, provides benzene phosphonous acid compounds in which two to four benzene nuclei are bound together and which contain one to three phosphorus atoms of the formula:

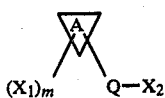 (I)

wherein
m is 1 or 2, A is unsubstituted or substituted diphenyl or terphenyl,
Q is a single bond or an unsubstituted or substituted phenylene radical, $X_1$ is a radical of formula

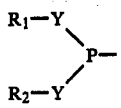

and
$X_2$ is hydrogen or a radical of formula

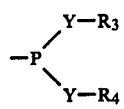 (IIa)

$R_1$, $R_2$, $R_3$ and $R_4$ are, independently, hydrogen or unsubstituted or a substituted hydrocarbon radical, containing up to 16 carbon atoms,
Y is oxygen, sulfur or a radical of formula

 (III)

and
Z, either bound to R, together with N-atom, forms a hetero cyclic ring or is the same as $R_1$, $R_2$, $R_3$ or $R_4$, are produced by the reaction of a compound of formula

 (IV)

wherein
Hal is halogen and $X_3$ is hydrogen or a radical of formula

—P(Hal)$_2$ (V)

with so many mols per mol of the compound of formula (IV) of a compound of formula $R_1$—Y—H (VI)

or of a mixture of 2, 3 or 4 compounds of formulae $R_1$—Y—H, $R_2$—Y—H, $R_3$—Y—H and $R_4$—Y—H, as Hal-radicals are present in the compound of formula (IV).

However, these phosphonites have not been entirely satisfactory in their stabilizing effect.

In accordance with the present invention, hindered bisphenol diphosphonites are provided having the structure:

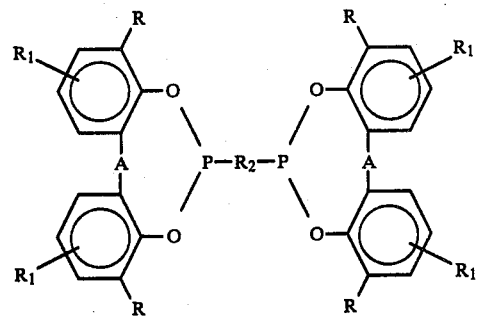

wherein:
A is selected from the group consisting of thio sulfur —S—; oxy oxygen —O—; alkylidene having from one to about ten carbon atoms; cycloalkylidene having from about four to about eight carbon atoms; and phenylalkylidene having from seven to about twelve carbon atoms;
R is selected from the group consisting of alkyl having from one to about eighteen carbon atoms; cycloalkyl having from three to about twelve carbon atoms; and aralkyl having from seven to about twelve carbon atoms;
$R_1$ is selected from the group consisting of hydrogen; alkyl having from one to about eighteen carbon atoms; cycloalkyl having from three to about twelve carbon atoms; and aralkyl having from seven to about twelve carbon atoms;
$R_2$ is selected from the group consisting of

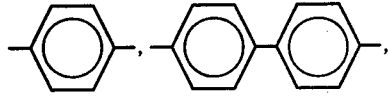

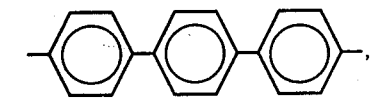

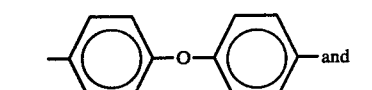

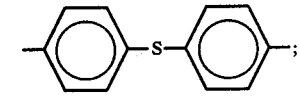

as well as synthetic resin compositions having an enhanced resistance to deterioration by heat and light comprising a synthetic resin and such phosphonites.

Exemplary A alkylidene include methylene, ethylidene, isopropylidene, butylidene, isobutylidene, amylidene, hexylidene, heptylidene, octylidene, nonylidene, decylidene, undecylidene, and dodecylidene; exemplary A cycloalkylidene include cyclopropylidene, cyclobutylidene, cyclopentylidene, cyclohexylidene, cycloheptylidene, cyclooctylidene; exemplary aryl alkylidene include benzylidene, phenethylidene, phenpropylidene, phenbutylidene, phenamylidene, phenhexylidene, and isopropylbenzylidene.

Exemplary R and $R_1$ alkyl groups having from one to about eighteen carbon atoms include methyl, ethyl, propyl, isopropyl, butyl, secondary butyl, tertiary butyl, isobutyl, amyl, isoamyl, tertiary amyl, hexyl, isohexyl, heptyl, octyl, 2-ethylhexyl, isooctyl, tertiary octyl, nonyl, decyl, undecyl, dodecyl, tridecyl, tetradecyl, hexadecyl and octadecyl.

Exemplary R and $R_1$ cycloalkyl having about three to about twelve carbon atoms include cyclopropyl, cyclobutyl, cyclopentyl, cyclohexyl, cycloheptyl, cyclooctyl, cyclododecyl and α-methylcyclohexyl.

Exemplary R and $R_1$ aralkyl groups having from seven to about twelve carbon atoms include benzyl, α-methylbenzyl, α,α-dimethyl benzyl, phenpropyl, phenbutyl, phenamyl, and phenhexyl.

The hindered bisphenol diphosphites are derived from hindered bisphenols of the structure:

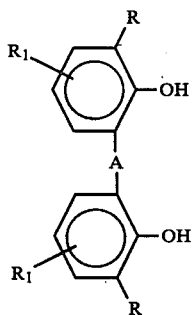

Exemplary such hindered bisphenols include 2,2'-methylenebis(4-methyl-6-t-butylphenol), 2,2'-methylenebis (4-ethyl-6-t-butylphenol), 2,2'-methylenebis(4,6-di-t-butylphenol), 2,2'-methylenebis[4-methyl-6-(α-methylcyclohexyl)phenol], 2,2'-n-butylidenebis(4,6-dimethylphenol), bis-1,1-(2'-hydroxy-3',5'-dimethylphenyl)-3,5,5-tri-methylhexane, 2,2'-cyclohexylidenebis(4-ethyl-6-t-butylphenol), 2,2'-isopropylbenzylidene-bis(4-ethyl-6-t-butylphenol), 2,2'-thiobis(4-t-butyl-6-methylphenol), 2,2'-thiobis(4-methyl-6-t-butylphenol), 2,2'-thiobis(4,6-di-t-butylphenol), 2,2'-methylenebis(4-α-methylbenzyl-6-cyclohexylphenol), 2,2'-methylenebis(4-cyclohexyl-6-α-methylbenzylphenol), 2,2'-ethylidenebis(4-methyl-6-t-butylphenol), 2,2'-ethylidenebis(4-sec-butyl-6-butylphenol), bis(2-hydroxy-3-t-butylphenyl) ether and bis(2-hydroxy-3-propylphenyl) ether.

Typical phosphonites of the invention are as follows:

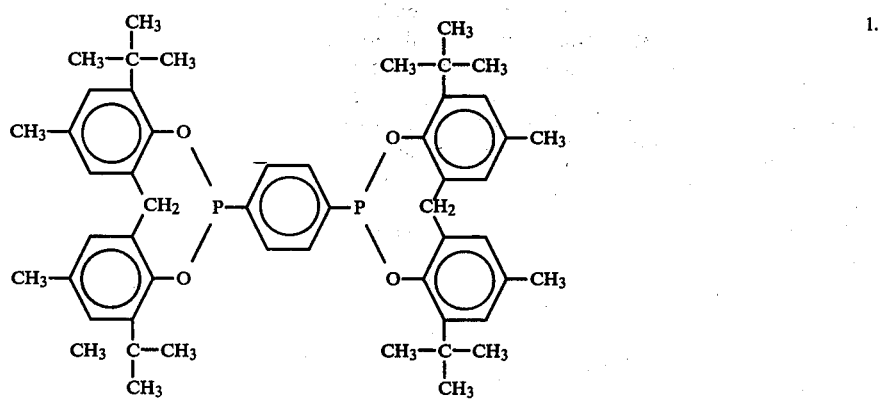

1. Bis(4,4'-dimethyl-6,6'-di-t-butyl-2,2'-methylene diphenyl) phenylene-diphosphonite

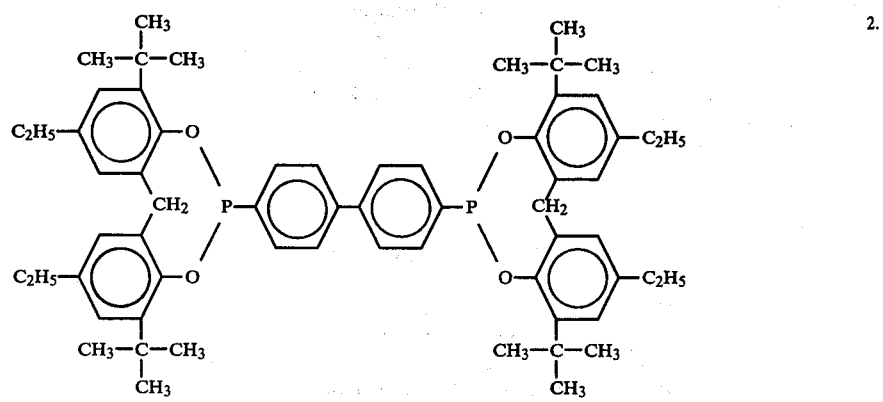

2. Bis(4,4'-diethyl-6,6'-di-t-butyl-2,2'-methylenediphenyl) bi-phenylene-diphosphonite -continued
3.
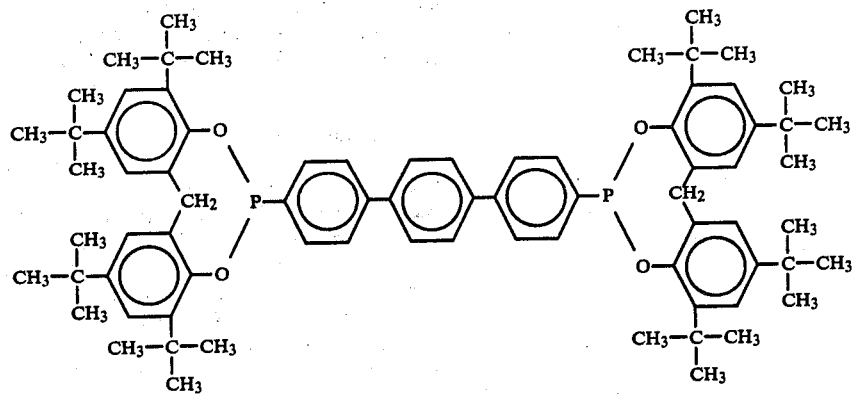
Bis(4,4',6,6'-tetra-t-butyl-2,2'-methylenediphenyl) terphenylene-diphosphonite
4.
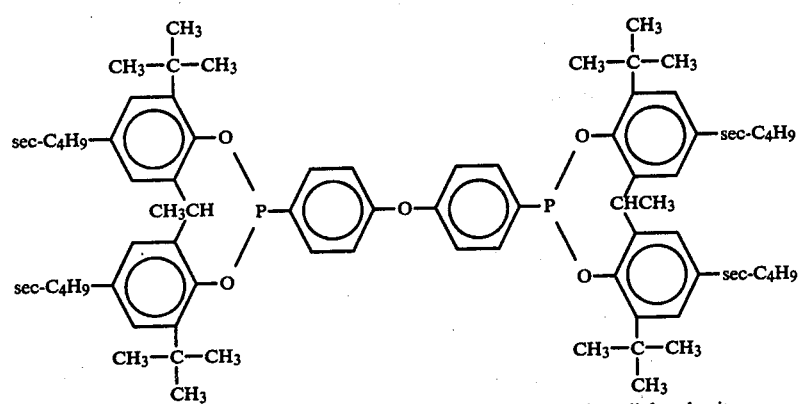
Bis(4,4'-di-sec-butyl-6,6'-di-t-butyl-2,2'-ethylidenediphenyl) oxydiphenylene-diphosphonite
5.
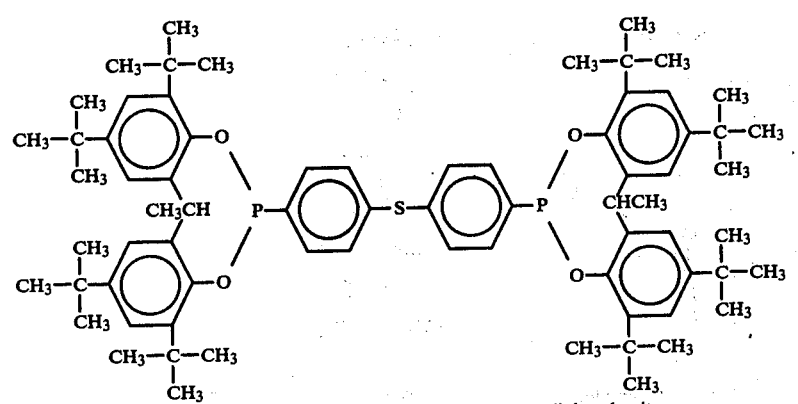
Bis(4,4',6,6'-tetra-t-butyl-2,2'-ethylidenediphenyl) thiodiphenylene-diphosphonite
6.
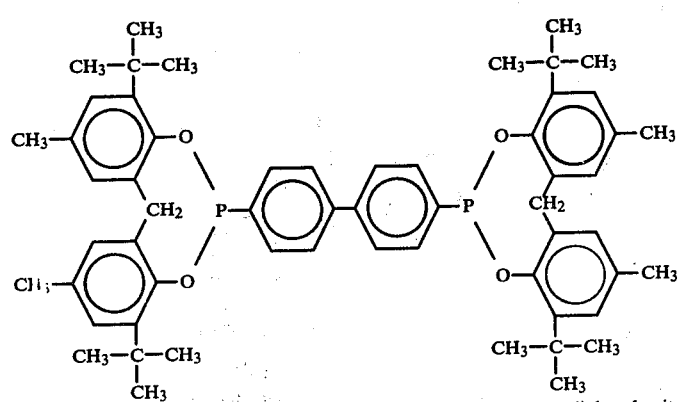
Bis(4,4'-dimethyl-6,6'-di-t-butyl-2,2'-methylenediphenyl) biphenylene-diphosphonite -continued
7.
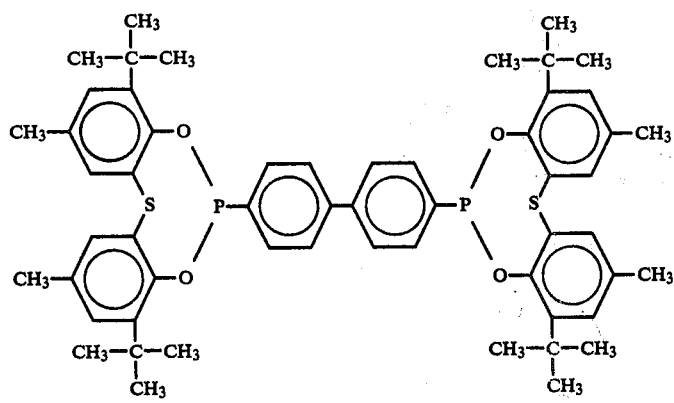
Bis(4,4'-dimethyl-6,6'-di-t-butyl-2,2'-thiodiphenyl) biphenylene-diphosphonite
8.
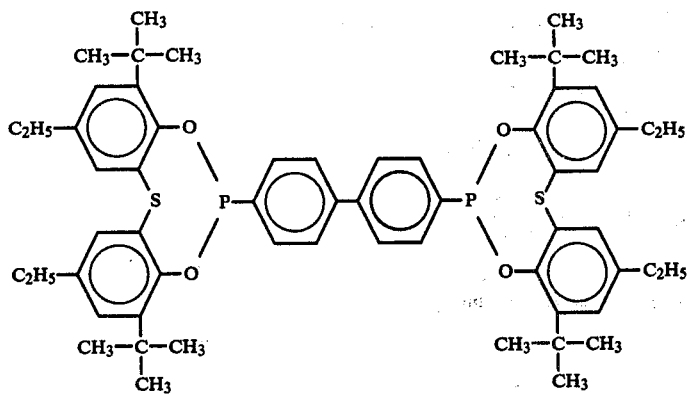
Bis(4,4'-diethyl-6,6'-di-t-butyl-2,2'-thiodiphenyl) biphenylene-diphosphonite
9.
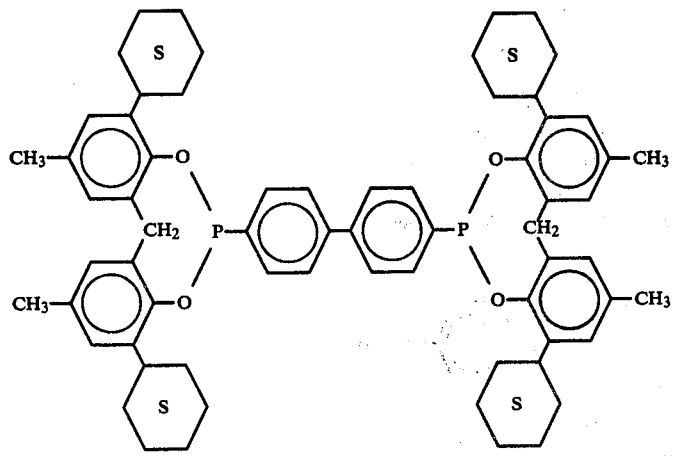
Bis(4,4'-dimethyl-6,6'-dicyclohexyl-2,2'-methylene diphenyl) biphenylene-diphosphonite 10.
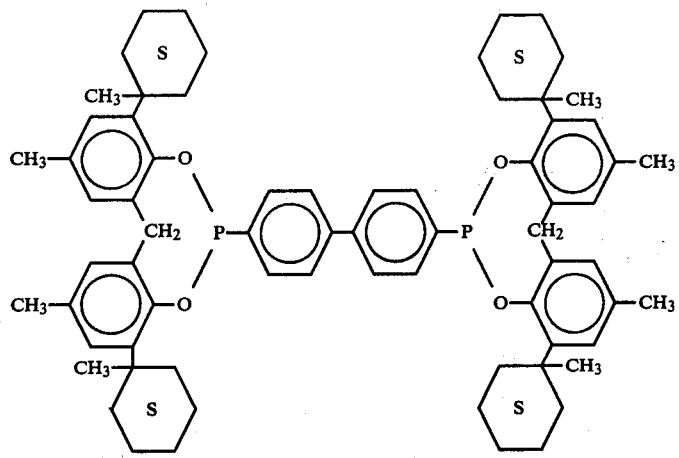
Bis[4,4'-dimethyl-6,6'-bis(α-methyl-cyclohexyl)-2,2'-methylenediphenyl]biphenylene-diphosphonite
11.
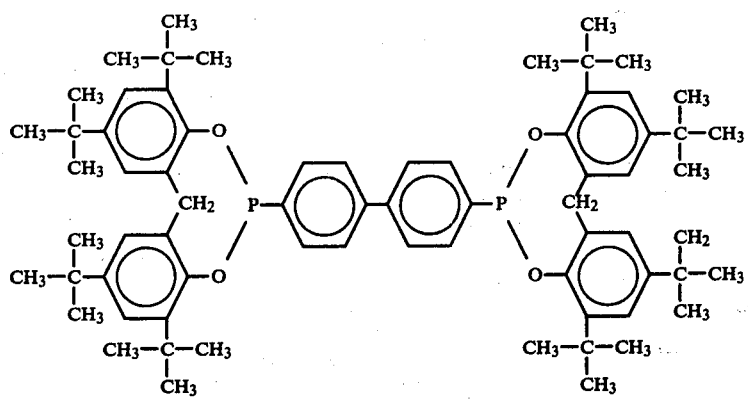
Bis(4,4'-6,6'-tetra-t-butyl-2,2'-methylenediphenyl) biphenylene-diphosphonite
12.
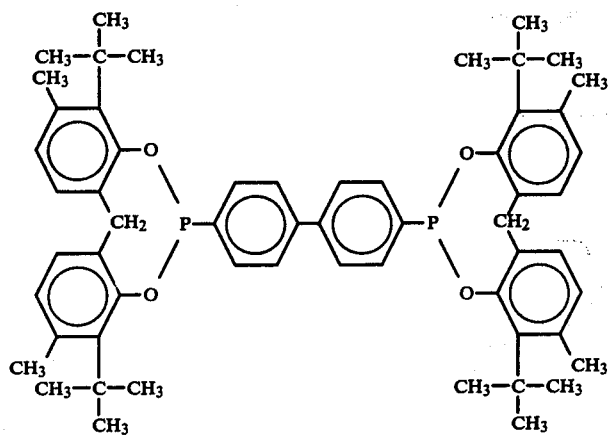
Bis(5,5'-dimethyl-6,6'-di-t-butyl-2,2'-methylene diphenyl) biphenylene-diphosphonite
13.
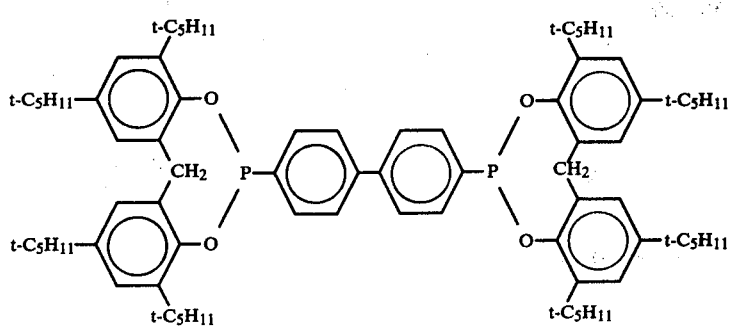

-continued
bis(4,4',6,6'-tetra-t-amyl-2,2'-methylenediphenyl) biphenylene diphosphonite

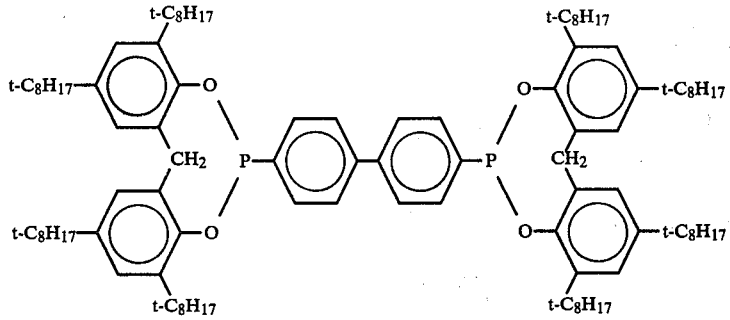

Bis(4,4'-6,6'-tetra-t-octyl-2,2'-methylenediphenyl) biphenylene diphosphonite

These phosphonites are readily prepared by conventional procedures. Thus, for example, the corresponding bisphenol

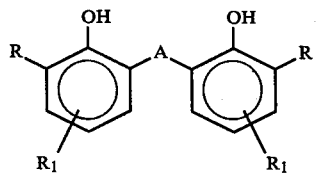

can be reacted with $Cl_2P—R_2—PCl_2$ in the presence of a base, such as an amine, to form the phosphonite.

The following Example serves to illustrate the procedure:

EXAMPLE I

Preparation of bis(4,4'-diethyl-6,6'-di-t-butyl-2,2'-methylenediphenyl) biphenylene diphosphonite

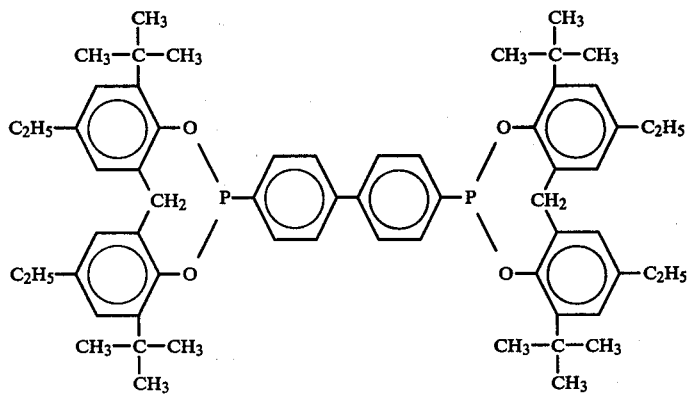

To a solution of 200 ml toluene and 7.12 g 4,4'-biphenyl (bisdichlorophosphine), 13.62 g of 2,2'-methylenebis(4-methyl-6-t-butylphenol) was added at 5° C. Then, 9.72 g of triethylamine was added dropwise at 0° to 5° C., and the whole was stirred for 6 hours at 86° C. The hydrochloric acid salt of triethylamine was filtered out, and solvent was stripped from the reaction mixture. A glassy solid, m.p. 157° to 161° C., was obtained.

Small amounts of the hindered bisphenol diphosphonites of this invention when combined with synthetic resin improve the light stability of the resin. The amount of the hindered bisphenol disphosphonites is generally within the range from about 0.01 to about 10 parts by weight, preferably from about 0.1 to about 5 parts by weight, per 100 parts by weight of resin.

Synthetic resins that can have their resistance to deterioration enhanced with hindered bisphenol diphosphonites according to this invention include α-olefin polymers such as polyethylene, polypropylene, polybutene-1, poly-3-methylbutene-1, and copolymers thereof, such as copolymers of ethylene, propylene and butene-1 with each other and with other copolymerizable mixtures thereof, such as ethylenevinyl acetate copolymer; ethylene-propylene copolymer; polystyrene; polyvinyl acetate; polyacrylic esters; copolymers from styrene and another monomer (for example, maleic anyhydride, butadiene, and acrylonitrile); acrylonitrilebutadienestyrene copolymer, acrylic acid ester-butadienestyrene copolymer, methacrylic acid ester-butadiene-styrene copolymer, polymethacrylate esters such as polymethacrylate; polyvinyl alcohol; polyvinyl formal; polyvinyl butyral; polyphenyleneoxides; linear polyesters such as polyethyleneterephthalate and polybutyleneterephthalate; polyamides such as polycaprolactam and polyhexamethyleneadipamide; polycarbonates; polyacetals; polyurethanes; cellulosic resins; phenol-formaldehyde resins; urea-formaldehyde resins; melamine-formaldehyde resins; epoxy resins; unsaturated polyester resins; silicon resins; halogen-containing resins such as polyvinyl chloride, polyvinyl bromide, polyvinyl fluoride, polyvinylidene chloride, polyvinylidene fluoride, and copolymers thereof, chlorinated polyethylene, chlorinated polypropylene, copolymers of vinylchloride with other copolymerizable monomers such as vinyl acetate, ethylene, propylene, styrene, isobutene, vinylidene chloride, maleic anhydride, acrylonitrile, butadiene, isoprene, acrylic esters and maleic esters; and rubbers such as polyisoprene rubber, polybutadiene rubber, epichlorohydrin rubber, chloroprene rubber, chlorinated rubber and blends of any of the above.

The hindered bisphenol diphosphonites of the invention can be combined with conventional heat stabilizers such as phenolic antioxidants, polyvalent metal salts of organic acids, organic phosphites, thioesters, and other known heat stabilizers, thereby constituting light and heat stabilizer compositions of the invention.

The phenolic antioxidant contains one or more phenolic hydroxyl groups, and one or more phenolic nuclei, and can contain from about eight to about three hundred carbon atoms. In addition, the phenolic nucleus can contain an oxy or thio ether group.

The alkyl-substituted phenols and polynuclear phenols, because of their molecular weight, have a higher boiling point, and therefore are preferred because of their lower volatility. There can be one or a plurality of alkyl groups of one or more carbon atoms. The alkyl group or groups including any alkylene groups between phenol nuclei preferably aggregate at least four carbon atoms. The longer the alkyl or alkylene chain, the better the compatibility with polypropylene, inasmuch as the phenolic compound then acquires more of an aliphatic hydrocarbon character, and therefore there is no upper limit on the number of alkyl carbon atoms. Usually, from the standpoint of availabilty, the compound will not have more than about eighteen carbon atoms in an alkyl, alicyclidene and alkylene group, and a total of not over about fifty carbon atoms. The compounds may have from one to four alkyl radicals per phenol nucleus.

The phenol contains at least one and preferably at least two phenolic hydroxyls, the two or more hydroxyls being in the same ring, if there is only one. In the case of bicyclic phenols, the rings can be linked by thio or oxyether groups, or by alkylene, alicyclidene or arylidene groups.

The monocyclic phenols which can be employed have the structure:

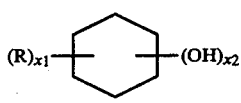

R is selected from the group consisting of hydrogen; halogen; and organic radicals containing from one to about thirty carbon atoms, such as alkyl, aryl, aklenyl, alkaryl, aralkyl, cycloalkenyl, cycloalkyl, alkoxy, and acyl

where
R' is aryl, alkyl or cycloalkyl.

$x_1$ and $x_2$ are integers from one to four, and the sum of $x_1$ and $x_2$ does not exceed six.

The polycyclic phenol phenol is one having at least two aromatic nuclei linked by a polyvalent linking radical, as defined by the formula:

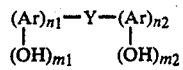

wherein
Y is a polyvalent linking group selected from the group consisting of oxygen; carbonyl; sulfur; sulfinyl; aromatic, aliphatic and cycloaliphatic hydrocarbon groups; and oxyhydrocarbon, thiohydrocarbon and heterocyclic groups. The linking group can have from one up to twenty carbon atoms.

Ar is a phenolic nucleus which can be a phenyl or a polycarbocyclic group having condensed or separate phenyl rings; each Ar group contains at least one free phenolic hydroxyl group up to a total of five. The Ar rings can also include additional rings connected by additional linking nuclei of the type Y, for example, Ar—Y—Ar—Y—Ar.

$m_1$ and $m_2$ are numbers from one to five, and $n_1$ and $n_2$ are numbers of one or greater, and preferably from one to four.

The aromatic nucleus Ar can, in addition to phenolic hydroxyl groups, include one or more inert substituents. Examples of such inert substituents include hydrogen, halogen atoms, e.g., chlorine, bromine and fluorine; organic radicals containing from one to about thirty carbon atoms, such as alkyl, aryl, alkaryl, aralkyl, cycloalkenyl, cycloalkyl, alkoxy, aryloxy and acyloxy

where R' is aryl, alkyl or cycloalkyl, or thiohydrocarbon groups having from one to about thirty carbon atoms, and carboxyl

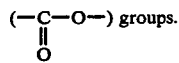 groups.

Usually, however, each aromatic nucleus will not have more than about eighteen carbon atoms in any hydrocarbon substituent group. The Ar group can have from one to four substituent groups per nucleus.

Typical aromatic nuclei include phenyl, naphthyl, phenanthryl, triphenylenyl, anthracenyl, pyrenyl, chrysenyl, and fluoroenyl groups.

When Ar is a benzene nucleus, the polyhydric polycyclic phenol has the structure:

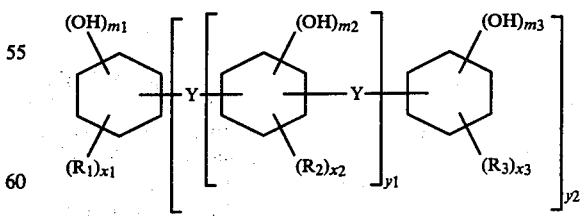

wherein
$R_1$, $R_2$ and $R_3$ are inert substituent groups as described in the previous paragraph;
$m_1$ and $m_3$ are integers from one to a maximum of five;
$m_2$ is an integer from one to a maximum of four;

$x_1$ and $x_3$ are integers from zero to four, and
$x_2$ is an integer from zero to three;
$y_2$ is an integer from zero to about six and
$y_2$ is an integer from one to five, preferably one or two.

Preferably, the hydroxyl groups are located ortho and/or para to Y.

Exemplary Y groups are alkylene, alkylidene, and alkenylene; arylene, alkyl arylene, arylalkylene; cycloalkylene, cycloalkylidene; and oxa- and thia-substituted such groups; tetrahydrofuranes, esters and triazino groups. The Y groups are usually bi, tri, or tetravalent, connecting two, three or four Ar groups. However, higher valency Y groups connecting more than four Ar groups, can also be used. According to their constitution, the Y groups can be assigned to subgenera as follows:

(1) Y groups where at least one carbon in a chain or cyclic arrangement connect the aromatic groups, such as:

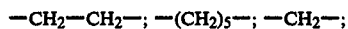

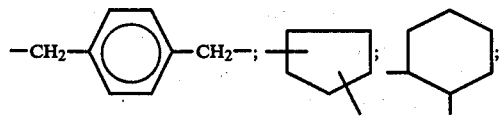

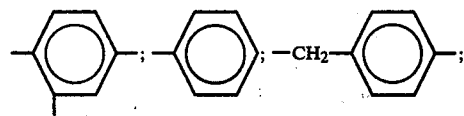

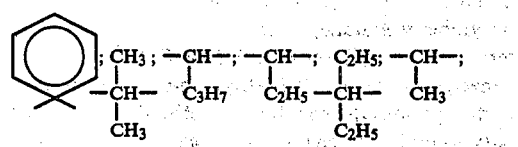

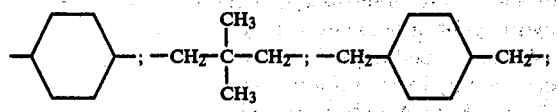

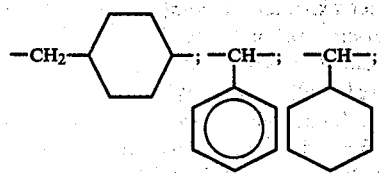

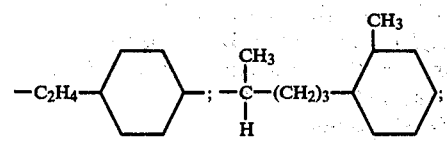

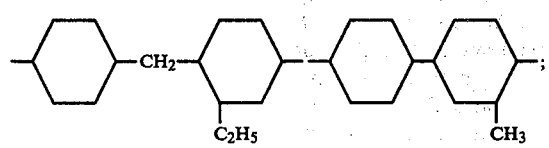

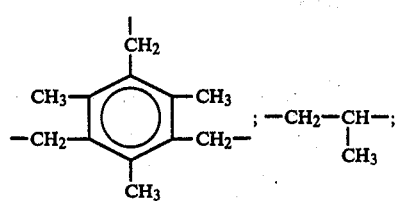

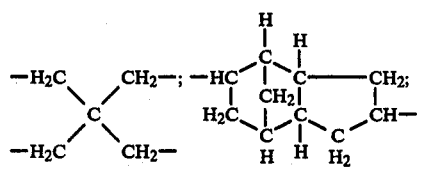

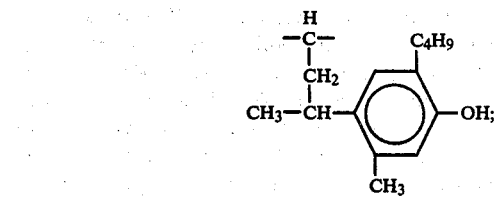

(2) Y groups where only atoms other than carbon link the aromatic rings, such as —O—, —S—,

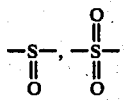

and —(S)$_x$— where x is a number from one to ten;

(3) Y groups made up of more than a single atom including both carbon and other atoms linking the aromatic nuclei, such as:

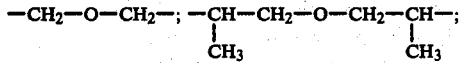

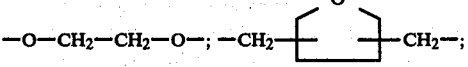

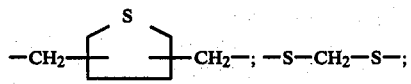

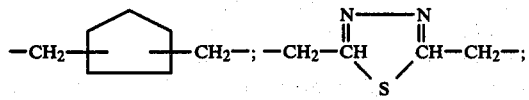

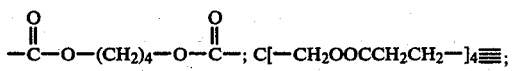

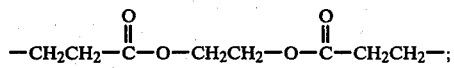

-continued

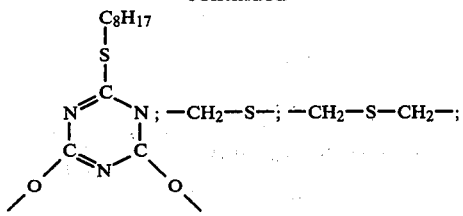

and

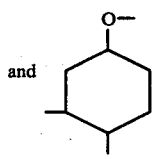

Although the relation of effectiveness to chemical structure is insufficiently understood, many of the most effective phenols have Y groups of subgenus (1), and accordingly this is preferred. Some of these phenols can be prepared by the alkylation of phenols or alkyl phenols with polyunsaturated hydrocarbons such as dicyclopentadiene or butadiene.

Representative phenols include guaiacol, resorcinol monoacetate, vanillin, butyl salicylate, 2,6-di-tert-butyl-4-methyl phenol, 2-tert-butyl-4-methoxy phenol, 2,4-dinonyl phenol, 2,3,4,5-tetradecyl phenol, tetrahydro-α-naphthol, o-, m- and p-cresol, o-, m- and p-phenyl-phenol, o-, m- and p-xylenols, the carvenols, symmetrical xylenol, thymol, o-, m- and p-nonylphenol, o-, m- and p-dodecyl-phenol, and o-, m- and p-octyl-phenol, o-, and m-tert-butyl-p-hydroxy-anisole, p-n-decyloxy-phenol, p-n-decyloxy-cresol, nonyl-n-decyloxycresol, eugenol, isoeugenol, glyceryl monosalicylate, methyl-p-hydroxy-cinnamate, 4-benzyloxy-phenol, p-acetylaminophenol, p-stearyl-aminophenol, methyl-p-hydroxybenzoate, p-di-chlorobenzoyl-aminophenol, p-hdroxysalicyl anilide, stearyl-(3,5-di-methyl-4-hydroxy-benzyl)thioglycolate, stearyl-β-(4-hydroxy-3,5-di-t-butylphenyl)propionate, distearyl-3,5-di-t-butyl-4-hydroxybenzylphosphonate, and distearyl (4-hydroxy-3-methyl-5-t-butyl) benzylmalonate.

Exemplary polyhydric phenols are orcinol, propyl gallate, catechol, resorcinol, 4-octyl-resorcinol, 4-dodecylresorcinol, 4-octadecyl-catechol, 4-isooctyl-phloroglucinol, pyrogallol, hexahydroxybenzene, 4-isohexylcatechol, 2,6-ditertiary-butyl-resorcinol, 2,6-di-isopropyl-phloroglucinol.

Exemplary polyhydric polycyclic phenols are methylene bis-(2,6-di-tertiary-butyl-phenol), 2,2-bis-(4-hydroxy phenyl)propane, methylene-bis-(p-cresol), 4,4'-benzylidene bis (2-tertiary-butyl-5-methyl-phenol), 4,4'-cyclo-hexylidene bis-(2-tertiary-butylphenol), 2,2'-methylene-bis-(4-methyl-6-(1'-methyl-cyclohexyl)-phenol), 2,6-bis-(2'-hydroxy-3'-tertiary-butyl-5'-methyl-benzyl)-4-methylphenol, 4,4'-bis-(2-tertiary-butyl-5-methyl-phenol), 2,2'-bis-(4-hydroxy-phenyl)butane, ethylene bis-(p-cresol), 4,4'-oxobis-phenol, 4,4'-oxobis-(3-methyl-5-isopropyl-phenol), 4,4'-oxobis-(3-methyl-phenol), 2,2'-oxobis-(4-dodecyl-phenol), 2,2'-oxobis-(4-methyl-5-tertiary-butyl-phenol), 4,4'-thio-bis-phenol; 4,4'-thio-bis-(3-methyl-6-tertiary-butyl-phenol), 2,2'-thio-bis-(4-methyl-6-tertiary-butyl-phenol), 4,4'-n-butylidene-(2-t-butyl-5-methyl-phenol), 2,2'-methylene-bis-(4-methyl-6-(1'-methyl-cyclohexyl)phenol), 4,4'-cyclohexylene bis-(2-tertiary-butyl-phenol), 2,6-bis-(2'-hydroxy-3'-t-butyl-5'-methyl-benzyl)-4-methyl-phenol, 4,4'-oxobis(naphthalene-1,5-diol), 1,3'-bis-(naphthalene-2,5-diol) propane, and 2,2'-butylene bis-(naphthalene-2,7-diol), (3-methyl-5-tert-butyl-4-hydroxyphenyl)-4'-hydroxy-phenyl) propane, 2,2'-methylene-bis-(4-methyl-5-isopropylphenol), 2,2'-methylene-bis-(4-methyl-5-isopropylphenol), 2,2'-methylene-bis-(5-tert-butyl-4-chlorophenol), (3,5-di-tert-butyl-4-hydroxyphenyl)-(4'-hydroxyphenyl)ethane, (2-hydroxy-phenyl)-(3',5'-di-tert-butyl-4',4-hydroxyphenyl) ethane, 2,2'-methylene-bis-(4-octylphenol), 4,4'-propylene-bis-(2-tert-butyl-phenol), 2,2'-isobutylene-bis-(4-nonylphenol), 2,4-bis-(4-hydroxy-3-t-butyl-phenoxy)-6-(n-octylthio)-1,3,5-triazine, 2,4,6-tris-(4-hydroxy-3-t-butyl-phenoxy)-1,3,5-triazine, 2,2'-bis-(3-t-butyl-4-hydroxyphenyl) thiazolo-(5,4-d)thiazole, 2,2'-bis-(3-methyl-5-t-butyl-4-hydroxyphenyl)thiazolo-(5,4-d)-thiazole, 4,4'-bis-(4-hydroxyphenyl) pentanoic acid octadecyl ester, cyclopentylene-4,4'-bis-phenol, 2-ethylbutylene-4,4'-bisphenol, 4,4'-cyclooctylene-bis-(2-cyclohexylphenol), β,β-thiodiethanol-bis-(3-tert-butyl-4-hydroxyphenoxy acetate), 1,4-butanedio-bis-(3-tert-butyl-4-hydroxyphenoxy acetate), pentaerythritol tetra-(4-hydroxyphenol propionate), 2,4,4'-tri-hydroxy benzophenone, bis-(2-tert-butyl-3-hydroxy-5-methylphenyl) sulfide, bis-(2-tert-butyl-4-hydroxy-5-methylphenyl) sulfide, bis-(2-tert-butyl-4-hydroxy-5-methylphenyl)sulfoxide, bis-(3-ethyl-5-tert-butyl-4-hydroxybenzyl) sulfide, bis-(2-hydroxy-4-methyl-6-tert-butyl-phenyl)sulfide, 4,4'-bis-(4-hydroxyphenol) pentanoic acid octadecyl thiopropionate ester, 1,1,3-tris-(2'-methyl-4-hydroxy-5'-tert-butylphenyl)butane, 1,1,3-tris-(1-methyl-3-hydroxy-4-tert-butylphenyl) butane, 1,8-bis-(2-hydroxy-5-methyl-benzoyl-n-octane, 2,2'-ethylene-bis-[4'-(3-tert-butyl-4-hydroxyphenyl)-thiazole], 1-methyl-3-(3-methyl-5-tert-butyl-4-hydroxybenzyl)-naphthalene, 2,2'-(2-butene)-bis-(4-methoxy-6-tert-butylphenol)-bis-[3,3-bis-(4-hydroxy-3-t-butylphenyl) butyric acid] glycol ester, 4,4'-butylidene-bis-(6-t-butyl-m-cresol), 1,1,3-tris-(2-methyl-4-hydroxy-5-t-butylphenyl) butane, 1,3,5-tris-(3,5-di-t-butyl-4-hydroxybenzyl)-2,4,6-trimethylbenzene, tetrakis[methylene-3(3,5-di-t-butyl-4-hydroxyphenyl)propionate] methane, 1,3,5-tris-(3,5-di-t-butyl-4-hydroxybenzyl) isocyanurate, 1,3,5-tris-(3,5-di-t-butyl-4-hydroxyphenyl) propionyl-oxyethyl isocyanurate, 2-octylthio-4,6-di-(4-hydroxy-3,5-di-t-butyl) phenoxy-1,3,5-triazine, 4,4'-thiobis-(6-t-butyl-m-cresol) pentaerythritol hydroxyphenyl propionate, stearyl(3,5-dimethyl-4-hydroxybenzyl) thioglycolate, stearyl-β-(3,5-di-t-butyl-4-hydroxyphenyl) propionate, distearyl(4-hydroxy-3-methyl-5-t-butylbenzyl) malonate, 2,2'-methylenebis(4-methyl-6-t-butylphenol), 4,4'-methylenebis(2,6-di-t-butylphenol), bis[3,3-bis(4-hydroxy-3-t-butylphenyl) butylic acid] glycolester, 1,3,5-tris(2,6-dimethyl-3-hydroxy-4t-butylbenzyl) isocyanurate and bis [2-t-butyl-4-methyl-6-(2-hydroxy-3-t-butyl-5-methylbenzyl) phenyl] terephthalate.

A particularly desirable class of polyhydric polycyclic phenols are the dicyclopentadiene polyphenols, which are of the type:

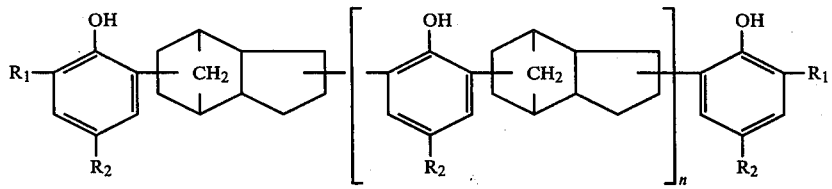

in which
- $R_1$ and $R_2$ are lower alkyl, and can be the same or different, and
- n is the number of the groups enclosed by the brackets, and is usually from 1 to about 5. These are described in U.S. Pat. No. 3,567,683, dated March 2, 1971 to Spacht. A commercially available member of this class is Wingstay L, exemplified by dicyclopentadiene tri-(2-tert-butyl-4-methyl-phenol) of the formula:

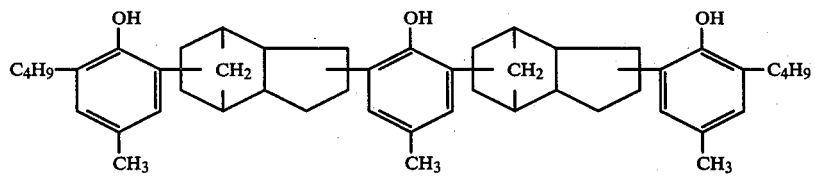

The polyhydric polycyclic phenols used in the invention can also be condensation products of phenols or alkylphenols with hydrocarbons having a bicyclic ring structure and a double bond or two or more double bonds, such as α-pinene, β-pinene, dipentene, limonene, vinylcyclohexene, dicyclopentadiene, allo-ocimene, isoprene and butadiene. These condensation products are usually obtained under acidic conditions in the form of more or less complex mixtures of monomeric and polymeric compounds. However, it is usually not necessary to isolate the individual constituents. The entire reaction product, merely freed from the acidic condensation catalyst and unchanged starting material, can be used with excellent results. While the exact structure of these phenolic condensation products is uncertain, the Y groups linking the phenolic nuclei all fall into the preferred subgenus 1. For method of preparation, see e.g., U.S. Pat. Nos. 3,124,555, 3,242,135, and British Pat. No. 961,504.

When the hindered bisphenol diphosphonites is used with a polyvalent metal salt of an organic acid, the organic acid will ordinarily have from about six to about twenty-four carbon atoms. The polyvalent metal can be any metal of Group II of the Periodic Table, such as zinc, calcium, cadmium, barium, magnesium and strontium. The alkali metal salts and heavy metal salts such as lead salts are unsatisfactory. The acid can be any organic non-nitrogenous monocarboxylic acid having from six to twenty-four carbon atoms. The aliphatic, aromatic, alicyclic and oxygen-containing heterocyclic organic acids are operable as a class. By the term "aliphatic acid" is meant any open chain carboxylic acid, substituted, if desired, with nonreactive groups, such as halogen, sulfur and hydroxyl. By the term "alicyclic" it will be understood that there is intended any cyclic acid in which the ring is nonaromatic and composed solely of carbon atoms, and such acids may if desired have inert, nonreactive substituents such as halogen, hydroxyl, alkyl radicals, alkenyl radicals and other carbocyclic ring structures condensed therewith. The oxygen-containing heterocyclic compounds can be aromatic or nonaromatic and can include oxygen and carbon in the ring structure, such as alkylsubstituted furoic acid. The aromatic acids likewise can have nonreactive ring substituents such as halogen, alkyl and alkenyl groups, and other saturated or aromatic rings condensed therewith.

As exemplary of the acids which can be used in the form of their metal salts there can be mentioned the following: hexoic acid, 2-ethylhexoic acid, n-octoic acid, isootoic acid, capric acid, undecylic acid, lauric acid, myristic acid, palmitic acid, margaric acid, stearic acid, oleic acid, ricinoleic acid, behenic acid, chlorocaproic acid, hydroxy capric acid, benzoic acid, phenylacetic acid, butyl benzoic acid, ethyl benzoic acid, propyl benzoic acid, hexyl benzoic acid, salicylic acid, naphthoic acid, 1-naphthalene acetic acid, orthobenzoyl benzoic acid, naphthenic acids derived from petroleum, abietic acid, dihydroabietic acid, hexahydrobenzoic acid, and methyl furoic acid.

The water-insoluble salts are preferred, because they are not leached out when the plastic is in contact with water. Where these salts are not known, they are made by the usual types of reactions, such as by mixing the acid, or anhydride with the corresponding oxide or hydroxide of the metal in a liquid solvent, and heating, if necessary, until salt formation is complete.

A variety of organic triphosphites and acid phosphites can be employed, of which the following are exemplary.

The organic triphosphite can be any organic phosphite having three or more organic radicals attached to phosphorus through oxygen. The acid phosphite can be any organic phosphite having one or two organic radicals attached to phosphorus through oxygen. These radicals can be monovalent radicals, in the case of the triphosphites, diphosphites and monophosphites.

The organic triphosphites in which the radicals are monovalent radicals can be defined by the formula:

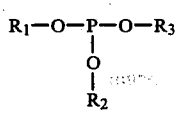

in which
- $R_1$, $R_2$ and $R_3$ are selected from the group consisting of alkyl, alkenyl, aryl, alkaryl, aralkyl, and cycloalkyl groups having from one to about thirty carbon atoms.

The acid phosphites are defined by the same formula, but one or two of $R_1$, $R_2$ and $R_3$ is hydrogen or a cation of a metal or ammonium.

Also included are the organic triphosphites having a bivalent organic radical forming a heterocyclic ring with the phosphorus of the type:

$$R_4 \diagdown_O^O \diagup P-O-R_5$$

in which $R_4$ is a bivalent organic radical selected from the group consisting of alkylene, arylene, aralkylene, alkarylene and cycloalkylene radicals having from two to about thirty carbon atoms, and $R_5$ is a monovalent organic radical as defined above in the case of $R_1$, $R_2$ and $R_3$;

$R_5$ is hydrogen or a cation, in the case of the acid phosphites.

Also useful organic triphosphites are mixed heterocyclic-open chain phosphites of the type:

$$R_4 \diagdown_O^O \diagup P-O-R_4-O-P \diagdown_O^O \diagup R_4$$

More complex triphosphites are formed from trivalent organic radicals, of the type:

$$R_6-O-P \diagdown_O^O \; HO-R_6 \diagdown_O^O \diagup P-O-R_6 \diagdown_O^O \diagup P-O-R_6 \diagup^{OH}_{OH}$$

in which $R_6$ is a trivalent organic radical of any of the types of $R_1$ to $R_5$, inclusive, as defined above.

A particularly useful class of complex triphosphites are the tetraoxadiphosphaspiro undecanes of the formula:

$$R_1-O-P \diagdown_{OCH_2}^{OCH_2} \diagup C \diagdown_{CH_2O}^{CH_2O} \diagup P-O-R_2$$

where $R_1$ and $R_2$ are selected from the group consisting of aryl, alkyl, aryloxyethyl, alkyloxyethyl, aryloxyethoxyethyl, alkyloxyethoxyethyl and alkyloxypolyethoxyethyl having from about 1 to about 30 carbon atoms.

In the case of the acid phosphites, one or both of $R_1$ and $R_2$ is also hydrogen or a cation.

An especially preferred class of organic triphosphites and acid phosphites have a bicyclic aromatic group attached to phosphorus through oxygen, with no or one or more phenolic hydroxyl groups on either or both of the aromatic rings. These phosphites are characterized by the formula:

$$POArO-P \diagdown_O^O \diagup \quad \text{or} \quad (HO)_m-Ar-O-P \diagdown_O^O \diagup$$

in which

Ar is a mono or bicyclic aromatic nucleus and m is an integer of from 0 to about 5. Z is one or a plurality of organic radicals as defined above for $R_1$ to $R_6$, taken singly or together in sufficient number to satisfy the valences of the two phosphite oxygen atoms.

One or both Z radicals is also hydrogen, in the case of the acid phosphites, and can include additional bicyclic aromatic groups of the type $(HO)_m$—Ar.

The cation in the case of acid phosphites can be a metal, such as an alkali metal, for instance, sodium, potassium or lithium; an alkaline earth metal, for instance, barium, calcium, or a nontoxic polyvalent metal, such as magnesium, tin and zinc.

Usually, the triphosphites and acid phosphites will not have more than about sixty carbon atoms.

Exemplary triphosphites are monophenyl di-2-ethylhexyl phosphite, diphenyl mono-2-ethylhexyl phsophite, di-isooctyl monotolyl phosphite, tri-2-ethylhexyl phosphite, phenyl dicyclohexyl phosphite, phenyl diethyl phosphite, triphenyl phosphite, tricresyl phosphite, tri(dimethylphenyl) phosphite, trioctadecyl phosphite, triisooctyl phosphite, tridodecyl phosphite, isooctyl diphenyl phosphite, diisooctyl phenyl phosphite, tri(t-octylphenyl) phosphite, tri-(t-nonylphenyl) phosphite, benzyl methyl isopropyl phosphite, butyl dicresyl phosphite, isooctyl di(octylphenyl) phosphite, di(2-ethylhexyl) (isooctylphenyl) phosphite, tri (2-cyclohexylphenyl) phosphite), tri-α-naphthyl phosphite, tri (phenylphenyl) phosphite, tri(2-phenylethyl) phosphite, ethylene phenyl phosphite, ethylene t-butyl phosphite, ethylene isohexyl phosphite, ethylene isooctyl phosphite, ethylene cyclohexyl phosphite, 2-phenoxy-1,3,2-dioxaphosphorinane, 2-butoxy-1,3,2-dioxyphosphorinane, 2-octoxy-5,5-dimethyl-dioxaphosphorinane, and 2-cyclohexyloxy-5,5-diethyl dioxaphosphorinane.

Exemplary pentaerythritol triphosphites are 3,9-diphenoxy-2,4,8,10-tetraoxa-3,9-diphosphaspiro-(5,5)-undecane (diphenyl-pentaerythritol diphosphite), 3,9-di(decyloxy)-2,4,8,10-tetraoxa-3,9-diphosphaspiro (5,5)-undecane, 3,9-di (isodecyloxy)-2,4,8,10-tetraoxa-3,9-diphosphaspiro-(5,5)-undecane, 3,9-di(octadecyloxy)-2,4,8,10-tetraoxa-3,9-diphosphaspiro-(5,5)-undecane, 3-phenoxy-9-isodecyloxy-2,4,8,10-tetraoxa-3,9-diphosphaspiro-(5,5)-undecane, 3,9-di (methoxy)-2,4,8,10-tetraoxa-3,9-diphosphaspiro-(5,5)-undecane, 3,9-di(-lauryloxy)-2,4,8,10-tetraoxa-3,9-diphosphaspiro-(5,5)-undecane, 3,9-di-p-tolyloxy-2,4,8,10-tetraoxa-3,9-diphosphaspiro-(5,5)-undecane, 3,9-di(methoxyethyloxy)-2,4,8,10-tetraoxa-3,9-diphosphaspiro-(5,5)-undecane, 3-methoxyethyloxy-9-isodecyloxy-2,4,8,10-tetraoxa-3,9-diphosphaspiro-(5,5)-undecane, 3,9-di(ethoxyethyloxy)-2,4,8,10-tetraoxa-3,9-diphosphaspiro-(5,5)-undecane, 3,9-di(butoxyethyloxy)-2,4,8,10-tetraoxa-3,9-diphosphaspiro-(5,5)-undecane, 3-methoxyethyloxy-9-butoxy-ethyloxy-2,4,8,10-tetraoxa-3,9-diphosphaspiro-(5,5)-undecane, 3,9-di(methoxyethoxyethyloxy)-2,4,8,10-tetraoxa-3,9-diphosphaspiro-(5,5)-undecane, 3,9-di-(butoxyethoxyethyloxy)-2,4,8,10-tetraoxa-3,9-diphosphaspiro-(5,5)-undecane, 3,9-di(methoxyethoxyethoxyethyloxy)-2,4,8,10-tetraoxa-3,9-diphosphaspiro- (5,5)-undecane, 3,9-di(methoxy(polyethoxy)ethyloxy)-2,4,8,10-tetraoxa-3,9-diphosphaspiro(5,5)-undecane where the (polyethoxy) ethyloxy group has an average molecular weight of 350),3,9-di(methoxy(polyethoxy)ethyloxy)-2,4,8,10-tetraoxa-3,9-diphosphaspiro-(5,5)-undecane (where the (polyethoxy) ethyloxy group has an average molecular weight of 550).

Exemplary of the bis aryl triphosphites are: bis(4,4'-thio-bis(2-tertiary-butyl-5-methyl-phenol)) isooctyl phosphite, mono(4,4'-thio-bis(2-tertiary-butyl-5-methyl-phenol)) di-phenyl phosphite, tri-(4,4'-n-butylidene-bis(2-tertiary-butyl-5-methylphenol)) phosphite, (4,4'-benzylidene-bis(2-tertiary-butyl-5-methyl-phenol)) di-phenyl phosphite, isooctyl 2,2'-bis(-parahydroxyphenyl) propane phosphite, decyl 4,4'-n-butylidene-bis (2-tertiary-butyl-5-methylphenol) phosphite, tri-4,4'-thio-bis (2-tertiary-butyl-5-methylphenol) phosphite, 2-ethylhexyl-2,2'-methylene-bis(4-methyl-6,1'-methylcyclohexyl) phenol phosphite, tri(2,2'-bis-(papa-hydroxyphenyl) propane) phosphite, tri(4,4'-thio-bis(2-tertiary-butyl-5-methyl-phenol) phosphite, isooctyl(2,6-bis(2'-hydroxy-3,5-dinonylbenzyl)-4-nonyl phenyl)) phosphite, tetra-tridecyl-4,4'-n-butylidene-bis(2-tertiary-butyl-5-methylphenyl) diphosphite, tetra-isooctyl-4,4'-thio-bis (2-tertiary-butyl-5-methylphenyl) diphosphite, 2,2'-methylenebis(4-methyl-6,1'-methyl cyclohexyl phenyl) polyphosphite, isooctyl-4,4'-isopropylidene-bisphenyl polyphosphite, 2-ethylhexyl-2,2'-methylene-bis(4-methyl-6,1'-methyl-cyclohexyl) phenyl triphosphite, tetra-tridecyl-4,4'-oxydiphenyl diphosphite, tetra-n-dodecyl-4,4'-n-butylidene bis (2-tertiarybutyl-5-methylphenyl) diphosphite, tetra-tridecyl-4,4'-isopropylidene bisphenyl diphosphite, hexa-tridecyl butane-1,1,3-tris(2'-methyl-5'-tertiary-butylphenyl-4') triphosphite.

Exemplary acid phosphites are di(phenyl) phosphite, monophenyl phosphite, mono(diphenyl) phosphite, dicresyl phosphite, di-(o-isooctylphenyl) phosphite, di(p-ethylhexylphenyl) phosphite, di(p-t-octylphenyl) phosphite, di(dimethylphenyl) phosphite, di-n-butyl phosphite, di-2-ethylhexyl phosphite, mono-2-ethylhexylphosphite, diisooctyl phosphite, monoisooctyl phosphite, monododecyl phosphite, 2-ethylhexyl phenyl phosphite, 2-ethylhexyl-(n-octylphenyl) phosphite, monocyclohexyl phosphite, dicyclohexyl phosphite, di(2-cyclohexyl phenyl) phosphite, di-$\alpha$-naphthyl phosphite, diphenyl phenyl phosphite, di(diphenyl) phosphite, di-(2-phenyl ethyl) phosphite, dibenzyl phosphite, monobenzyl phosphite, n-butyl cresyl phosphite and didodecyl phosphite, cresyl phosphite, t-octylphenyl phosphite, ethylene phosphite, butyl cresyl phosphite, isooctyl monotolyl phosphite and phenyl cyclohexyl phosphite.

Exemplary of the bis aryl acid phosphites are: bis(4,4'-thio-bis(2-tertiary-butyl-5-methylphenol)) phosphite, (4,4'-thio-bis(2-tertiary-butyl-5-methylphenol)) phenyl phosphite, bis(4,4'-n-butylidene-bis(2-tertiary-butyl-5-methylphenol)) phosphite, mono(4,4'-benzylidene-bis(2-tertiary-butyl-5-methylphenol)) phosphite, mono(2,2'-bis-(parahydroxyphenyl) propane) phosphite, mono(4,4'-butylidene-bis(2-tertiary-butyl-5-methylphenol) phosphite, bis(4,4'-thio-bis(2-tertiary-butyl-5-methylphenol)) phosphite, mono-2-ethylhexyl mono-2,2'-methylene-bis(4-methyl-6,1'-methylcyclohexyl) phenol phosphite, bis (2,2'-bis(para-hydroxyphenyl)propane) phosphite, monoisooctylmono(4,4'-thio-bis(2-tertiary-butyl-5-methylphenol)) phosphite, isooctyl-(2,6-bis(2'-hydroxy-3,5-dinonylbenzyl)-4-nonylphenyl)) phosphite, tri-tridecyl-4,4'-n-butylidene-bis(2-tertiary-butyl-5-methylphenyl) diphosphite, triisooctyl-4,4'-thio-bis(2-tertiary-butyl-5-methylphenyl) diphosphite, bis(2,2'-methylene-bis(4-methyl-6,1'-methyl cyclohexyl phenyl)) phosphite, isooctyl-4,4'-isopropylidene-bis-phenyl phosphite, monophenyl mono(2,2'-methylene-bis(4-methyl-6,1'-methyl-cyclohexyl)) triphosphite, di-tridecyl-4,4'-oxydiphenyl diphosphite, di-n-dodecyl-4,4'-n-butylidene-bis(2-tertiary-butyl-5-methylphenyl) diphosphite, di-tridecyl-4,4'-isopropylidene bisphenyl disphosphite, tetra-tridecyl butane-1,1,3-tris(2'-methyl-5-tertiary-butylphenyl-4)-triphosphite.

The thiodipropionic acid ester has the following formula:

$$R_1OOCCH_2CH_2-S-CH_2CH_2COOY$$

in which $R_1$ is an organic radical selected from the group consisting of hydrocarbon radicals such as alkyl, alkenyl, aryl, cycloalkyl and mixed alkyl aryl and mixed alkyl cycloalkyl radicals; hydroxyalkyl and hydroxyalkyloxyalkylene radicals; and esters thereof with aliphatic carboxylic acids; and Y is selected from the group consisting of (a) hydrogen, (b) a second R radical $R_2$, which can be the same as or different from the $R_1$ radical, (c) a polymeric chain of n thiodipropionic acid ester units:

$$-XO[OCCH_2CH_2SCH_2CH_2COOXO]_nOOCH_2CH_2-S-CH_2CH_2COOZ$$

where Z is hydrogen, $R_2$ or M, n is the number of thiodipropionic acid ester units in the chain, and X is a bivalent hydrocarbon group of the type of $R_1$, that is, alkylene, alkenylene, cycloalkylene, mixed alkylene-arylene and mixed alkylenecycloalkylene radicals; hydroxyalkylene and hydroxyalkyloxyalkylene radicals; and esters thereof with aliphatic carboxylic acids; the value of n can range upwards from 0, but there is no upper limit on n except as is governed by the ratio of carbon atoms to sulfur atoms as stated below; and (d) a polyvalent metal M of Group II of the periodic table such as zinc, calcium, cadmium, barium, magnesium and strontium.

The molecular weights of the R and Y radicals are taken such that with the remainder of the molecule the thiodipropionic ester has a total of from about ten to about sixty carbon atoms per sulfur atom.

Accordingly, the various thiodipropionic acid ester species coming within the above-designated categories within the general formula can be defined as follows:
 (a) $R_1OOCCH_2CH_2SCH_2CH_2COOH$
 (b) $R_1OOCCH_2CH_2SCH_2CH_2COOR_2$
 (c) $R_1O[OCCH_2CH_2SCH_2CH_2COOX-O]_nOCCH_2CH_2SCH_2CH_2COOZ$
 (d) $R_1OOCCH_2CH_2SCH_2CH_2COOM$ In the above formulae $R_1$ and $R_2$, M, X and Z are the same as before and the value of $n_1$ can range upwards from 1, but there is no upper limit on $n_1$ except as is imposed by the ratio of carbon atoms, as stated below. In the polymer (c), as in the other forms of thiodipropionic acid esters, the total number of carbon atoms per sulfur atom is within the range from about ten to about sixty.

The R radical of these esters is important in furnishing compatibility with the polymer. The Y radical is desirably a different radical, $R_2$ or M or a polymer, where R is rather low in molecular weight, so as to compensate for this in obtaining the optimum compatibility and nonvolatility. Where Y is a metal, the thiodipropionic acid ester furnishes the beneficial properties of the polyvalent metal salt which is described above.

The aryl, alkyl, alkenyl, and cycloalkyl groups may, if desired, contain inert, nonreactive substituents such as halogen and other carbocyclic and heterocyclic ring structures condensed therewith.

Typical R radicals are, for example, methyl, ethyl, propyl, isopropyl, butyl, isobutyl, t-butyl, amyl, isoamyl, n-octyl, isooctyl, 2-ethyl hexyl, t-octyl, decyl, dodecyl, octadecyl, allyl, hexenyl, linoleyl, ricinoleyl, oleyl, phenyl, xylyl, tolyl, ethylphenyl, naphthyl, cyclohexyl, benzyl, cyclopentyl, methylcyclohexyl, ethylcyclohexyl, and naphthenyl, hydroxyethyl, hydroxypropyl, glyceryl, sorbityl, pentaerythrityl, and polyoxyalkylene radicals such as those derived from diethylene glycol, triethylene glycol, polyoxypropylene glycol, polyoxyethylene glycol, and polyoxypropyleneoxyethylene glycol, and esters thereof with any of the organic acids named below in the discussion of the polyvalent metal salts, including in addition those organic acids having from two to five carbon atoms, such as acetic, propionic, butyric and valeric acids.

Typical X radicals are alkylene radicals such as ethylene, tetramethylene, hexamethylene, decamethylene, alkyl-substituted alkylene radicals such as 1,2-propylene,

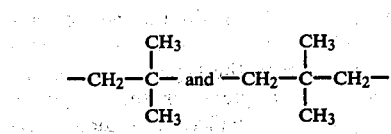

arylene radicals such as phenylene

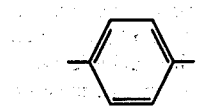

methylenephenylene

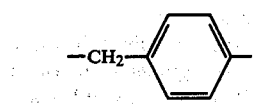

dimethylene phenylene

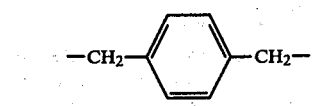

and alicyclylene such as cyclohexylene

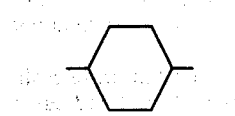

and cyclopentylene

As exemplary of the thiodipropionic acid esters which can be used, there can be mentioned the following: monolauryl thiodipropionic acid, dilauryl thiodipropionate, butyl stearyl thiodipropionate, 2-ethylhexyl lauryl thiodipropionate, di-2-ethylhexyl-thiodipropionate, diisodecyl thiodipropionate, isodecyl phenyl thiodipropionate, benzyl lauryl thiodipropionate, benzyl phenyl thiodipropionate, the diester of mixed coconut fatty alcohols and thiodipropionic acid, the diester of mixed tallow fatty alcohols and thiodipropionic acid, the acid ester of mixed cottonseed oil fatty alcohols and thiodipropionic acid, the acid ester of mixed soyabean oil fatty alcohols and thiodipropionic acid, cyclohexyl nonyl thiodipropionate, monooleyl thiodipropionic acid, hydroxyethyl lauryl thiodipropionate, monoglyceryl thiodipropionic acid, glyceryl monostearate monothiodipropionate, sorbityl isodecyl thiodipropionate, the polyester of diethylene glycol and thiodipropionic acid, the polyester of triethylene glycol and thiodipropionic acid, the polyester of hexamethylene glycol and thiodipropionic acid, the polyester of pentaerythritol and thiodipropionic acid, the polyester of octamethylene glycol and thiodipropionic acid, the polyester of p-dibenzyl alcohol and thiodipropionic acid, ethylbenzyl lauryl thiodipropionate, strontium stearyl thiodipropionate, magnesium oleyl thiodipropionate, calcium dodecylbenzyl thiodipropionate, and mono(dodecylbenzyl) thiodipropionic acid.

These esters are for the most part known compounds, but where they are not available, they are readily prepared by esterification of thiodipropionic acid and the corresponding alcohol.

Also useful are:

(1) Thioalkanoic acid amides of Tokuno et al Japanese Pat. No. 16,286/68 having the formula:

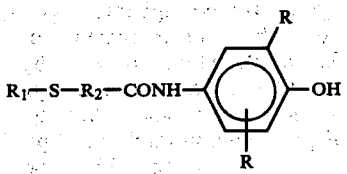

R is alkyl of one to eight carbon atoms, $R_1$ is alkyl of six to twenty-four carbon atoms, and $R_2$ is alkylene of one to six carbon atoms.

(2) Thioalkanoic acid amides of 1,3,5-triazines of Ozeki et al Japanese Pat. No. 20,366/68 having the formula:

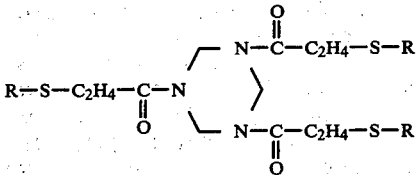

R is alkyl of eight to eighteen carbon atoms.

(3) Bis-thioalkanoic acid amides of Yamamoto et al Japanese Pat. No. 23,765/68 having the formula:

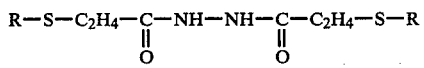

R is alkyl of more than six carbon atoms, aryl or aralkyl.

(4) Bis-thioalkylanoic acid amides of Ozeki et al Japanese Pat. No. 26,184/69 having the formula:

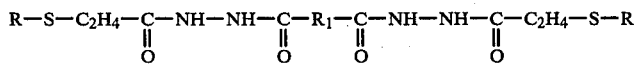

R is alkyl of twelve to eighteen carbon atoms, and $R_1$ is alkylene of one to ten carbon atoms, cycloalkylene, or arylene.

(5) Bis-alkylene thioalkanoic acid amides of Ozeki Japanese Pat. No. 31,464/69 having the formula:

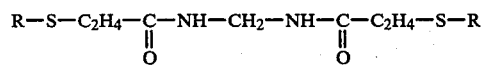

R is alkyl of more than six carbon atoms, aryl, or aralkyl.

(6) Thioalkanoic acid amide derivatives of Minagawa et al, published Japanese application No. 106,484/74 having the formula:

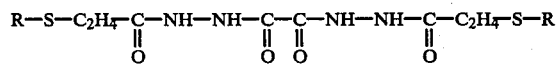

R is hydrocarbyl of one to twenty carbon atoms.

(7) Alkylene bis-thioalkanoic acid amides of U.S. Pat. No. 4,279,805 to Ohzeki et al, patented July 21, 1981, having the general formula:

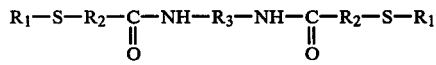

wherein:
$R_1$ is alkyl having from one to abut fifty carbon atoms;
$R_2$ is alkylene having from one to about three carbon atoms; and
$R_3$ is alkylene having from about two to about twelve carbon atoms.

$\beta$-Alkylthiopropionic acid esters having the general formula:

wherein:
R is alkyl of four to twenty carbon atoms;
n is a number from 1 to 6; and
R' is the residue of an alcohol having from one to six hydroxyl groups.

Pentaerythritol tetra dodecyl thio propionate is an example of this group.

Other conventional light stabilizers can be employed, such as 2-hydroxybenzophenones such as 2-hydroxy-4-methoxybenzophenone, 2,2'-dihydroxy-4-methoxybenzophenone, 2-hydroxy-4-n-octoxy benzophenone, 2,4-dihydroxybenzophenone, hydroxybenzyl, benzotriazoles, such as 2(2-hydroxy-5-methylphenyl) benzotriazoles, 2(2-hydroxy-3-t-butyl-5-methylphenyl)-5-chlorobenzotriazole, 2(2-hydroxy-3-5-di-t-butylphenyl)-5-chlorobenzotriazole, 2(2-hydroxy-3,5-di-t-amylphenyl) benzotriazole, and 2-[2-hydroxy-3,5-bis-($\alpha,\alpha$-dimethylbenzyl) phenyl] benzotriazole, benzoates and salicylates such as phenylsalicylate, 2,4-di-t-butylphenyl-3,5-di-t-butyl-4-hydroxy phenylbenzoate, hexadecyl-3,5-di-t-butyl-4-hydroxybenzoate, and p-t-butyl phenylsalicylate, nickel compounds such as nickel-2,2'-thiobis (4-t-octyl-phenolate), nickel-monoethyl(3,5-di-t-butyl-4-hydroxybenzyl) phosphonate, nickel-2,2-thiobis(4-t-octyl phenolate)-n-butylamine and (3,5-di-t-butyl-4-hydroxybenzyl) phosphonic acid monoethyl ester nickel salt, hindered amines such as 2,2,6,6-tetramethyl-4-piperidylbenzoate, (2,2,6,6-tetramethyl-4-piperidyl) sebacate, bis(1,2,2,6,6-pentamethyl-4-piperidyl) sebacate and tetrakis(2,2,6,6-tetramethyl-4-piperidyl) butanetetracarboxylate, substituted acrylonitriles such as methyl-$\alpha$-cyano-$\beta$-methyl-$\beta$-(p-methoxyphenyl) acrylate and oxalic anilides such as N-2-ethyl phenyl-N'-2-ethoxy-5-t-butyl phenyl oxalic diamide, N-2-ethyl phenyl-N'-2-ethoxy phenyl oxalic diamide.

A sufficient amount of the stabilizer or combination is used to improve the resistance of the synthetic polymer to deterioration in physical properties when exposed to heat and light, including, for example, discoloration, reduction in melt viscosity and embrittlement. Very small amounts are usually adequate. Amounts within the range from about 0.01 to about 10% total stabilizers including the hindered bisphenol diphosphonites by weight of the polymer are satisfactory. Preferably, from 0.1 to 5% is employed, for optimum stabilization.

The stabilizer systems of the invention are readily rendered in solid particulate form, comprising a blend of:
(a) hindered bisphenol diphosphonite stabilizer in an amount of from about 10 to about 35 parts by weight;
and optionally:
(b) a phenolic antioxidant in an amount from about 10 to about 35 parts by weight; and/or
(c) other heat or light stabilizers in an amount of from about 10 to about 35 parts by weight.

The hindered bisphenol diphosphonites of the invention can be employed in combination with phenolic antioxidant and/or other conventional heat and light stabilizers for the particular synthetic polymer.

Thus, for example, in the case of polyvinyl chloride resins, other polyvinyl chloride resin heat stabilizers can be included, including polyvalent metal fatty acid salts such as barium and cadmium salts of the higher fatty acids; organotin compounds; and epoxy compounds; and organic phosphites.

With polyolefin resins there can be employed fatty acid salts of polyvalent metals, and the higher fatty acid esters of thiodipropionic acids, such as, for example, dilauryl thiodipropionate.

With polyamide resin compositions, polyamide stabilizers such as copper salts in combination with iodides and/or other phosphorus compounds and salts of divalent manganese can be used.

With synthetic rubbers and acrylonitrile-butadienestyrene terpolymers, other antioxidants and polyvalent metal salts of the higher fatty acids can be used.

In addition, other conventional additives for synthetic polymers, such as plasticizers, lubricants, heavy metal diactivators, emulsifiers, antistatic agents, nucleating agents, flame-proofing agents, pigments and fillers, can be employed.

The stabilizer or combination is incorporated in the polymer in suitable mixing equipment, such as a mill or a Banbury mixer. If the polymer has a melt viscostiy which is too high for the desired use, the polymer can be worked until its melt viscosity has been reduced to the desired range before addition of the stabilizer. Mixing is continued until the mixture is substantially uniform. The resulting composition is then removed from the mixing equipment and brought to the size and shape desired for marketing or use.

The stabilized polymer can be worked into the desired shape, such as by milling, calendering, extruding or injection molding or fiber-forming. In such operations, it will be found to have a considerably improved resistance to reduction in melt viscosity during the heating, as well as a better resistance to discoloration and embrittlement on ageing and heating.

The following Examples illustrate preferred embodiments of stablizer systems and resin compositions containing phosphonites of the invention:

EXAMPLES 1 TO 8

Polypropylene compositions were prepared using phosphonites of the invention and having the following formulation:

| Ingredient | Parts by Weight |
|---|---|
| Unstabilized polypropylene | 100 |
| Dilaurylthiodipropionate | 0.2 |
| Ca stearate | 0.2 |
| Pentaerythritol tetrakis(3,5-di-t-butyl-4-hydroxyphenyl)propionate | 0.1 |
| Phosphonite as shown in Table I | 0.1 |

The composition was thoroughly blended and then extruded at 250° C. The mixture was then injection-molded at 250° C. to form sheets 1 mm thick.

Pieces 2.5 cm$^2$ were cut off from the sheets, and heated at 160° C. in a Geer oven to evaluate heat stability. The yellowness of the sheet after exposure to ultra-violet light for 72 hours was measured in a Hunter color difference meter. The composition was extruded five times and melt flow index (MFI) (at 230° C., load; 2160 g) was measured.

The results are shown in Table I.

TABLE I
| Example No. | Phosphonite | Heat Stability (Hours to Failure) | Yellowness % Original | Yellowness % After 72 Hours | MFI (g/10 min.) Extruded 1 time (MFI-1) | MFI (g/10 min.) Extruded 5 times (MFI-5) | MFI-5/ MFI-1 |
|---|---|---|---|---|---|---|---|
| Control 1 | None | 324 | 10.6 | 14.6 | 4.1 | 6.4 | 1.56 |
| Control 2 | 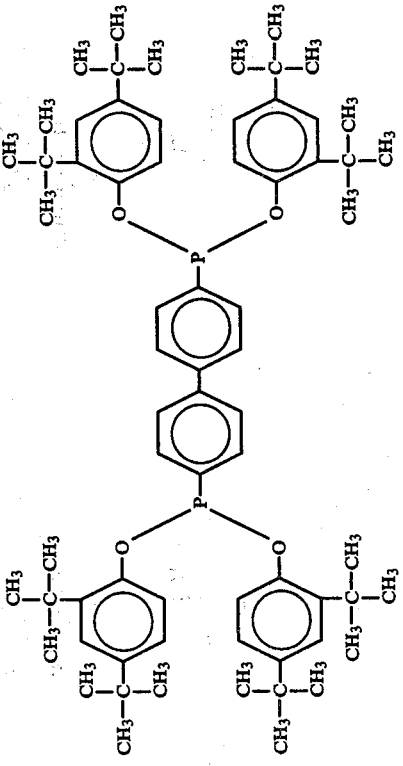 | 408 | 8.2 | 11.7 | 3.3 | 4.3 | 1.30 |
| Control 3 | 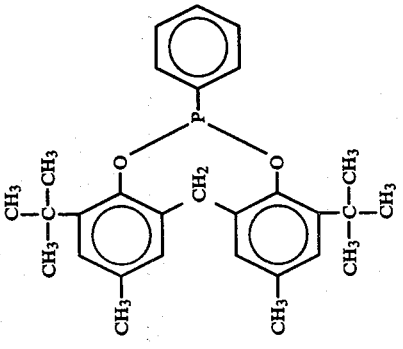 | 432 | 8.4 | 9.8 | 3.5 | 4.9 | 1.40 |

TABLE I-continued
| Example No. | Phosphonite | Heat Stability (Hours to Failure) | Yellowness % Original | Yellowness % After 72 Hours | MFI (g/10 min.) Extruded 1 time (MFI-1) | MFI (g/10 min.) Extruded 5 times (MFI-5) | MFI-5/MFI-1 |
|---|---|---|---|---|---|---|---|
| Control 4 | 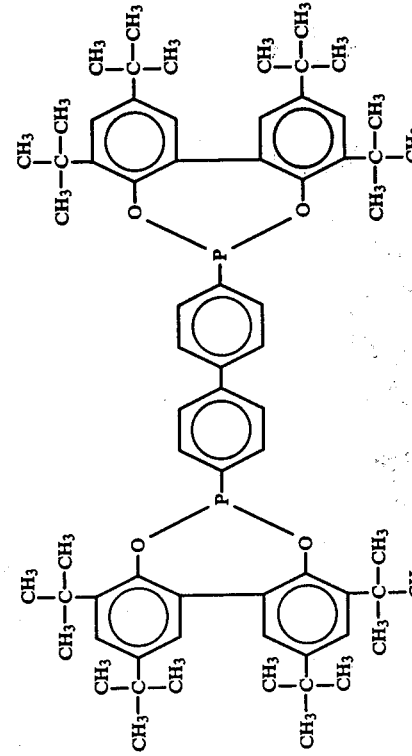 | 456 | 7.4 | 10.8 | 3.4 | 4.7 | 1.38 |
| Example 1 | 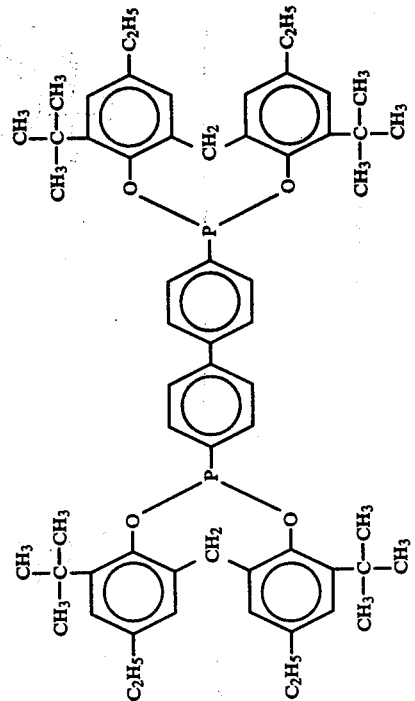 | 540 | 5.4 | 8.3 | 3.0 | 3.4 | 1.14 |

TABLE I-continued

| Example No. | Phosphonite | Heat Stability (Hours to Failure) | Yellowness % Original | Yellowness % After 72 Hours | MFI (g/10 min.) Extruded 1 time (MFI-1) | MFI (g/10 min.) Extruded 5 times (MFI-5) | MFI-5/ MFI-1 |
|---|---|---|---|---|---|---|---|
| Example 2 | (structure shown) | 528 | 6.5 | 7.5 | 3.3 | 4.0 | 1.22 |
| Example 3 | (structure shown) | 552 | 5.3 | 7.0 | 2.9 | 3.2 | 1.10 |

TABLE I-continued

| Example No. | Phosphonite | Heat Stability (Hours to Failure) | Yellowness % Original | Yellowness % After 72 Hours | MFI (g/10 min.) Extruded 1 time (MFI-1) | MFI (g/10 min.) Extruded 5 times (MFI-5) | MFI-5/MFI-1 |
|---|---|---|---|---|---|---|---|
| Example 4 | (structure) | 540 | 6.3 | 9.0 | 3.3 | 4.1 | 1.24 |
| Example 5 | (structure) | 552 | 5.7 | 8.9 | 3.2 | 3.9 | 1.22 |

TABLE I-continued
| Example No. | Phosphonite | Heat Stability (Hours to Failure) | Yellowness % Original | Yellowness % After 72 Hours | MFI (g/10 min.) Extruded 1 time (MFI-1) | MFI (g/10 min.) Extruded 5 times (MFI-5) | MFI-5/ MFI-1 |
|---|---|---|---|---|---|---|---|
| Example 6 | 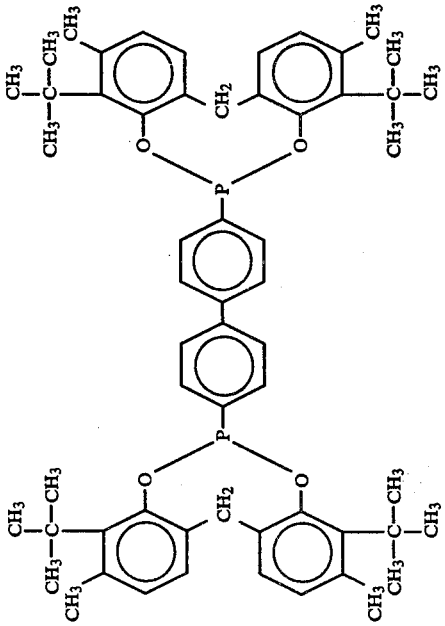 | 552 | 5.5 | 7.7 | 3.2 | 4.0 | 1.25 |
| Example 7 | 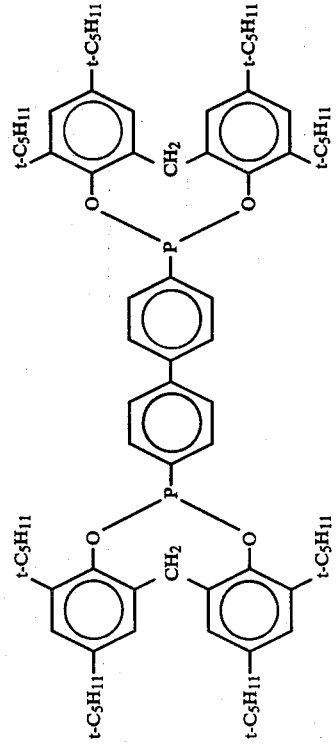 | 528 | 6.5 | 7.2 | 3.1 | 3.6 | 1.16 |

TABLE I-continued
| Example No. | Phosphonite | Heat Stability (Hours to Failure) | Yellowness % Original | Yellowness % After 72 Hours | MFI (g/10 min.) Extruded 1 time (MFI-1) | MFI (g/10 min.) Extruded 5 times (MFI-5) | MFI-5/ MFI-1 |
|---|---|---|---|---|---|---|---|
| Example 8 | 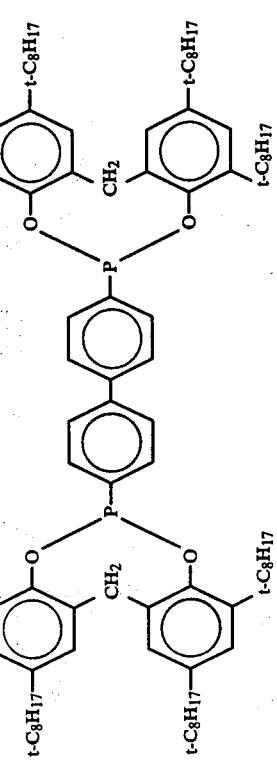 | 516 | 5.3 | 7.7 | 3.2 | 3.8 | 1.19 |

The superior effectiveness of the phosphonites of the invention, as compared to the Controls, in formulations otherwise the same, is apparent from the data.

EXAMPLES 9 TO 16

High-density polyethylene compositions were prepared using phosphonites of the invention, and having the following formulation:

| Ingredient | Parts by Weight |
|---|---|
| High-density polyethylene (Hizex 5100E) | 100 |
| Dilaurylthiodipropionate | 0.3 |
| Stearyl 3(3-5-di-t-butyl-4-hydroxyphenyl)propionate | 0.1 |
| Phosphonite as shown in Table II | 0.05 |

The stabilizers were blended with the polymer on a two-roll mill at 150° C. for five minutes, and sheets 1.2 mm thick were prepared by compression molding of the blend at 150° C. and 180 kg/cm$^2$ pressure for five minutes.

Pieces 10×20 mm were cut off from the sheets, and heated at 150° C. in a Geer oven on aluminum foil.

The time in hours when degradation set in, as determined by a significant discoloration and/or embrittlement, was noted as hours to failure.

The results are reported in Table II.

TABLE II

| Example No. | Phosphonite | Hours to Failure |
|---|---|---|
| Control 1 | None | 264 |
| Control 2 | 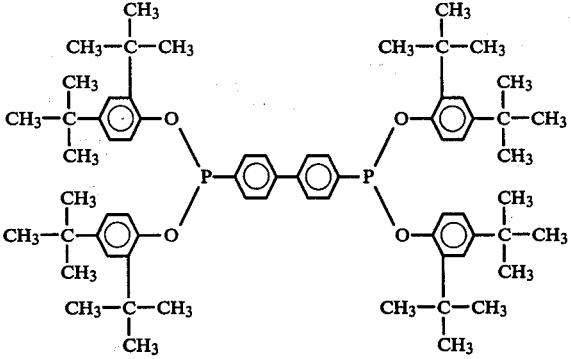 | 420 |
| Control 3 | 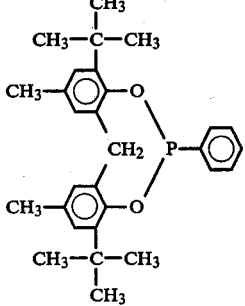 | 408 |
| Control 4 | 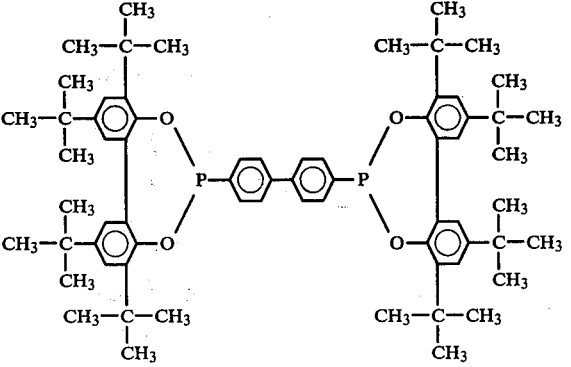 | 432 |

TABLE II-continued

| Example No. | Phosphonite | Hours to Failure |
|---|---|---|
| Example 9 | (structure) | 576 |
| Example 10 | (structure) | 600 |
| Example 11 | (structure) | 624 |
| Example 12 | (structure) | 624 |

TABLE II-continued

| Example No. | Phosphonite | Hours to Failure |
|---|---|---|
| Example 13 | 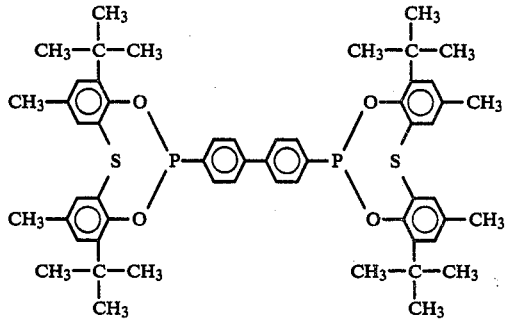 | 624 |
| Example 14 | 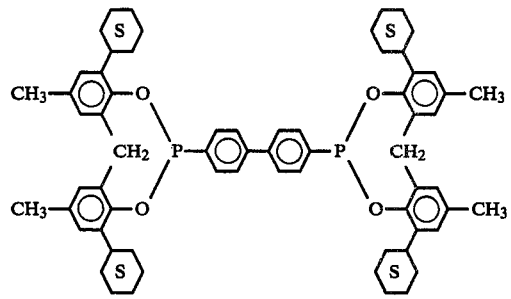 | 588 |
| Example 15 | 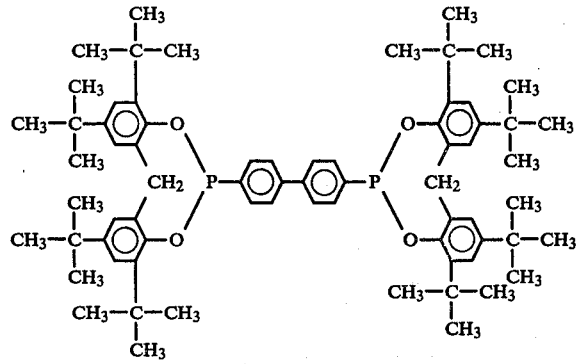 | 624 |
| Example 16 | 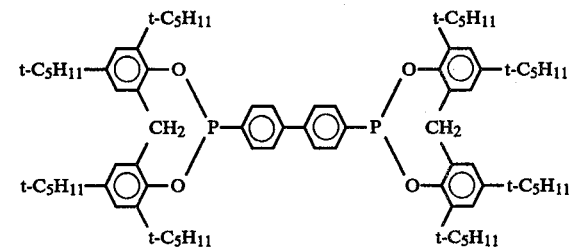 | 576 |

The superior effectiveness of the phosphonites of the invention, as compared to the Controls, in formulations otherwise the same, is apparent from the data.

EXAMPLES 17 TO 21

Polyphenylene oxide resin compositions having the following formulation were prepared:

| Ingredient | Parts by Weight |
|---|---|
| Poly(2,6-dimethyl-1-4-phenyleneoxide) | 48 |
| Polystyrene | 50 |
| Polycarbonate | 2 |
| $TiO_2$ | 3 |
| Phosphonite as shown in Table III | 0.5 |

The ingredients were mixed and then extruded at 60 rpm and 260° C., followed by injection-molding at 290° C., to prepare the test pieces. The heat stability was evaluated by heating and test pieces in a Geer oven at 125° C. for 100 hours. Elongation and Izod impact strength were measured before and after the heating, and the percent elongation and percent Izod impact strength retained were calculated.

The results are shown in Table III.

TABLE III
| Example No. | Phosphonite | % Elongation Retained | % Impact Strength Retained |
|---|---|---|---|
| Control 1 | 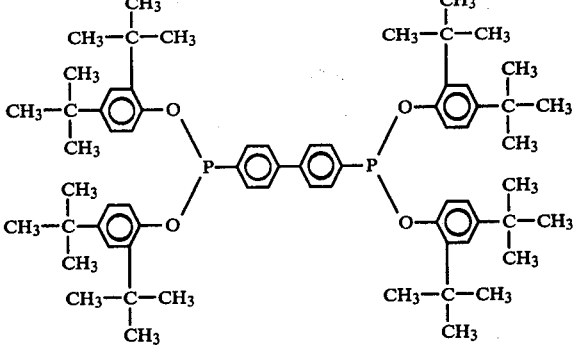 | 47 | 44 |
| Control 2 | 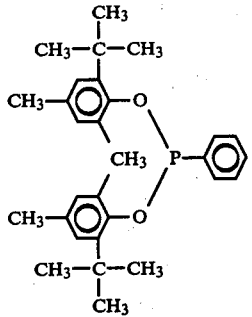 | 45 | 47 |
| Control 3 | 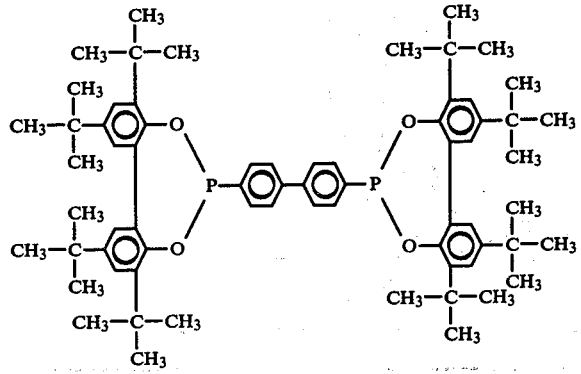 | 48 | 46 |
| Example 17 | 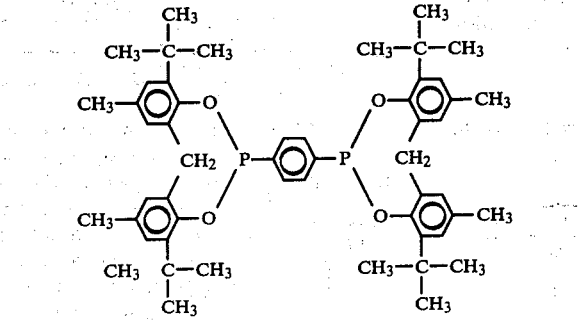 | 68 | 70 |

TABLE III-continued

| Example No. | Phosphonite | % Elongation Retained | % Impact Strength Retained |
|---|---|---|---|
| Example 18 | 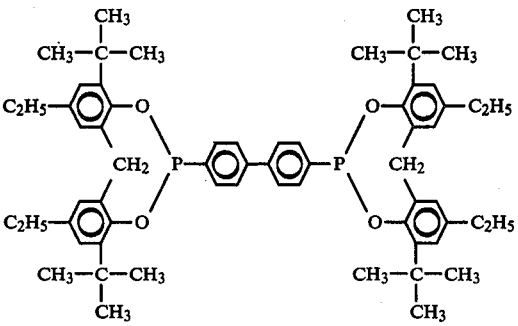 | 75 | 68 |
| Example 19 | 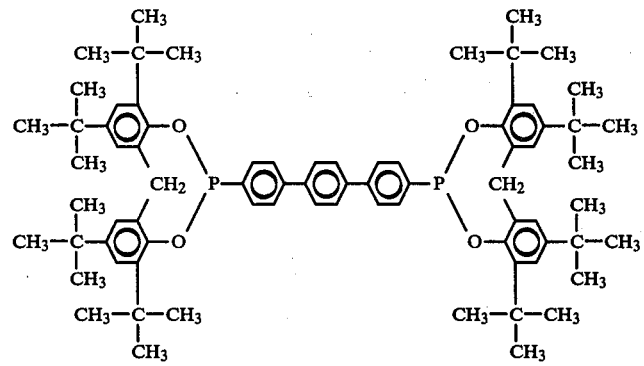 | 72 | 67 |
| Example 20 | 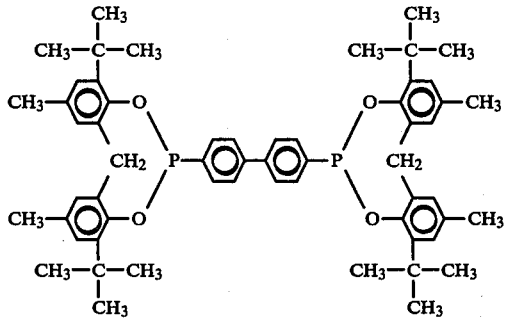 | 75 | 72 |
| Example 21 | 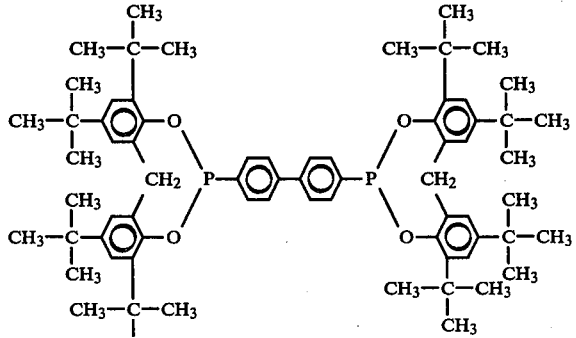 | 70 | 70 |

The superior effectiveness of the phosphonites of the invention, as compared to the Controls, in formulations otherwise the same, is apparent from the data.

EXAMPLES 22 TO 31

Acrylonitrile-butadiene-styrene terpolymer resin compositions were prepared using phosphonites of the invention and having the following formulation:

| Ingredient | Parts by Weight |
| --- | --- |
| Acrylonitrile-butadiene-styrene terpolymer (Blendex 111) | 100 |
| Zinc stearate | 0.5 |
| Tris(3,5-di-t-butyl-4-hydroxyphenyl propionyl oxyethyl)isocyanurate | 0.1 |
| Phosphonite as shown in Table IV | 0.3 |

The stabilizers were blended with the resin on a two-roll mill followed by compression molding at 160° C. of the resulting blend to prepare sheets 0.5 mm thick.

Heat stability was evaluated by heating the specimen sheets at 135° C. in a Geer oven for twenty hours. The whiteness of the specimens was evaluated using a Hunter color difference meter.

The results are shown in Table IV.

TABLE IV

| Example No. | Phosphonite | Whiteness |
| --- | --- | --- |
| Control 1 | None | 18 |
| Control 2 | 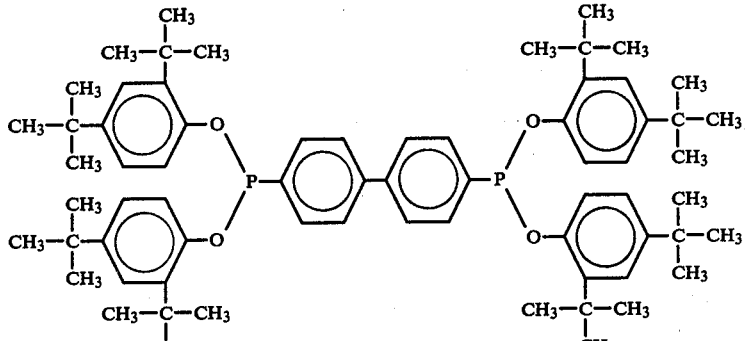 | 31 |
| Control 3 | 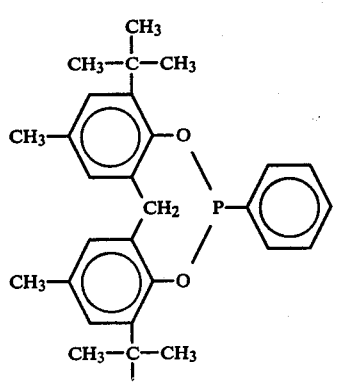 | 35 |
| Control 4 | 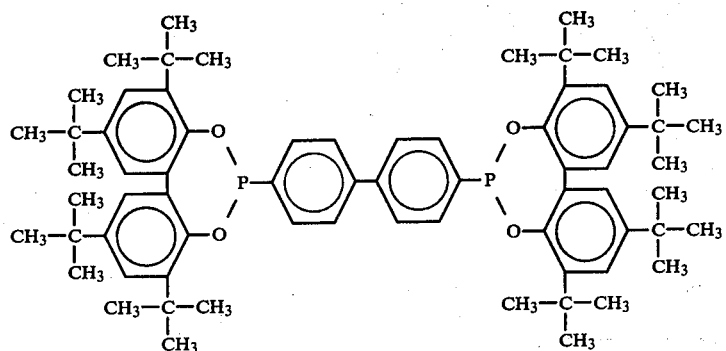 | 33 |

TABLE IV-continued

| Example No. | Phosphonite | Whiteness |
|---|---|---|
| Example 22 | (structure) | 48 |
| Example 23 | (structure) | 46 |
| Example 24 | (structure) | 44 |
| Example 25 | (structure) | 49 |

TABLE IV-continued
| Example No. | Phosphonite | Whiteness |
|---|---|---|
| Example 26 | 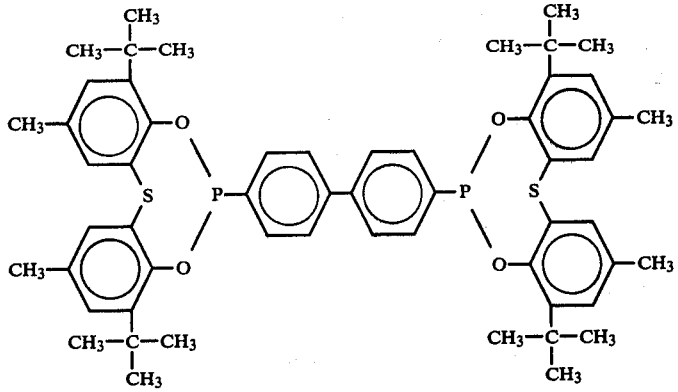 | 49 |
| Example 27 | 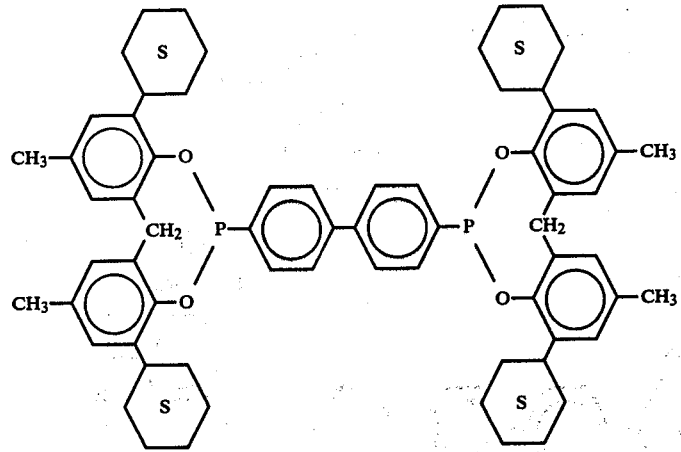 | 45 |
| Example 28 | 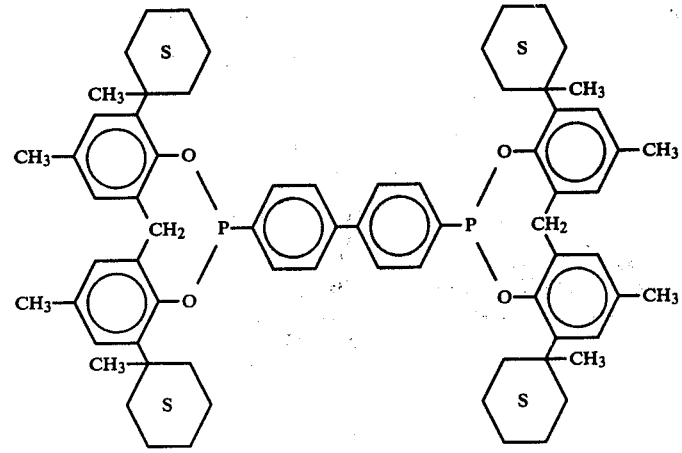 | 47 |

TABLE IV-continued

| Example No. | Phosphonite | Whiteness |
|---|---|---|
| Example 29 | (structure) | 44 |
| Example 30 | (structure) | 47 |
| Example 31 | (structure) | 47 |

The superior effectiveness of the phosphonites of the invention, as compared to the Controls, in formulations otherwise the same, is apparent from the data.

EXAMPLES 32 TO 39

A group of polyvinyl chloride resin compositions was prepared having the following formulation:

| Ingredient | Parts by Weight |
|---|---|
| Polyvinyl chloride (Geon 103 EP) | 100 |
| Dioctyl phthalate | 42 |
| Epoxidized soybean oil | 3 |
| Zn stearate | 0.3 |
| Ba stearate | 0.5 |
| Stearic acid | 0.3 |
| Phosphonite shown in Table V | 0.2 |

This formulation was blended and sheeted off on a two-roll mill at 175° C. for five minutes and then compression-molded at 180° C. to form clear sheets 1 mm thick.

The sheets were heated in air in a Geer oven at 190° C. to evaluate heat stability, and the time in minutes noted for the sheet to develop a noticeable discoloration and/or embrittlement.

Wet heat stability was also determined by heating at 175° C. in an atmosphere at 100% relative humidity, and again minutes to the development of a noticeable discoloration noted.

The results are shown in Table V.

TABLE V
| Example No. | Phosphonite | Heat stability at 190° C. (minutes to failure) | Wet heat stability at 175° C. (minutes to failure) |
|---|---|---|---|
| Control 1 | None | 40 | 60 |
| Control 2 | 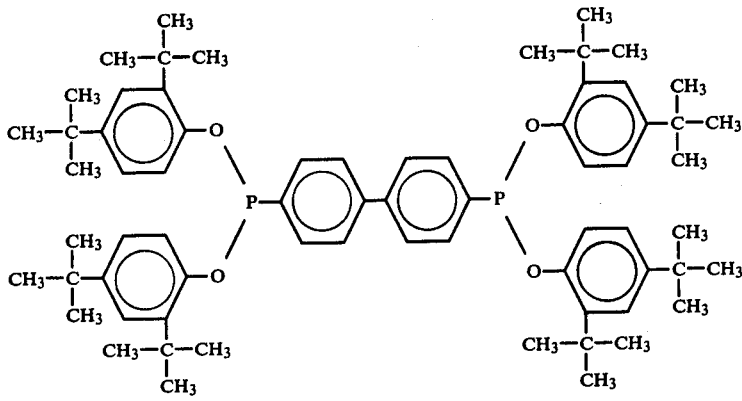 | 90 | 100 |
| Control 3 | 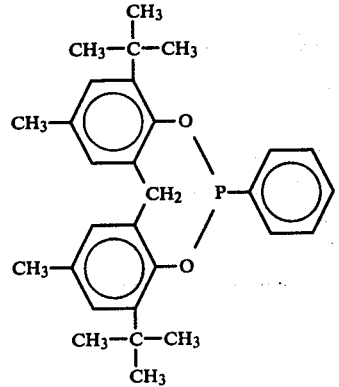 | 100 | 110 |
| Control 4 | 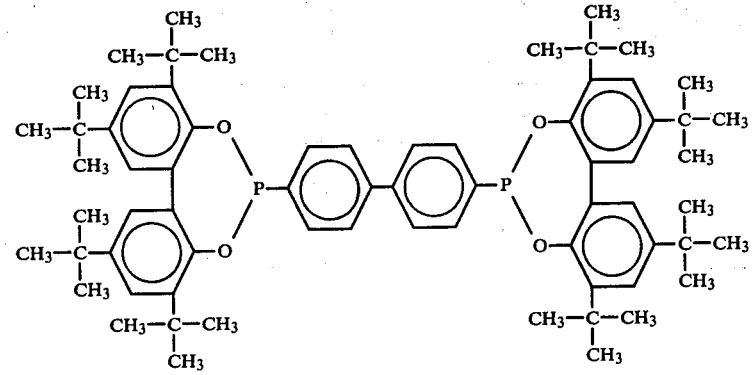 | 95 | 105 |

TABLE V-continued

| Example No. | Phosphonite | Heat stability at 190° C. (minutes to failure) | Wet heat stability at 175° C. (minutes to failure) |
|---|---|---|---|
| Example 32 | [structure] | >120 | >120 |
| Example 33 | [structure] | >120 | >120 |
| Example 34 | [structure] | >120 | >120 |

TABLE V-continued

| Example No. | Phosphonite | Heat stability at 190° C. (minutes to failure) | Wet heat stability at 175° C. (minutes to failure) |
| --- | --- | --- | --- |
| Example 35 | (structure) | >120 | >120 |
| Example 36 | (structure) | >120 | >120 |
| Example 37 | (structure) | >120 | >120 |

TABLE V-continued

| Example No. | Phosphonite | Heat stability at 190° C. (minutes to failure) | Wet heat stability at 175° C. (minutes to failure) |
|---|---|---|---|
| Example 38 | 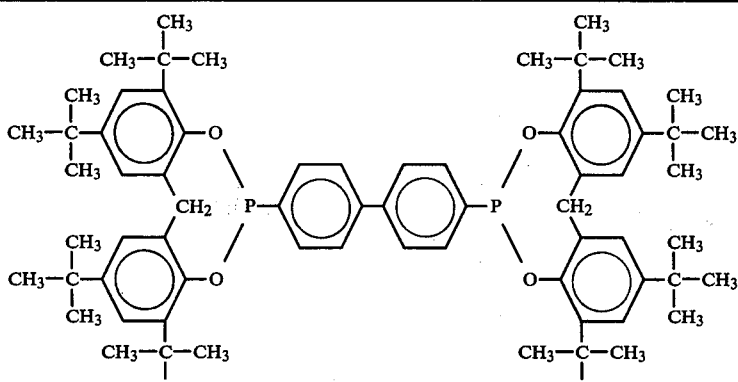 | >120 | >120 |
| Example 39 | 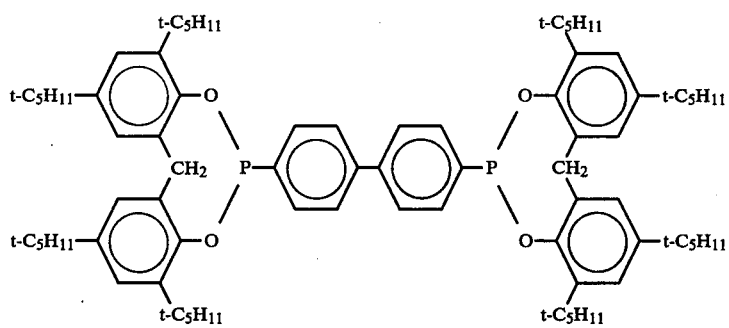 | >120 | >120 |

The superior effectiveness of the phosphonites of the invention, as compared to the Controls, in formulations otherwise the same, is apparent from the data.

EXAMPLES 40 TO 45

Ethylene-vinyl acetate copolymer resin compositions were prepared using phosphonites of the invention and having the following formulation:

| Ingredient | Parts by Weight |
|---|---|
| Ethylene-vinyl acetate copolymer resin | 100 |
| Montan wax | 0.3 |
| Stearyl-3-(3,5-di-t-butyl-4-hydroxyphenyl)propionate | 0.05 |
| Phosphonites as shown in Table VI | 0.1 |

The stabilizers were blended with the resin on a two-roll mill, and sheeted off.

Samples of the sheets were heated in a Geer oven at 175° C. and the time in minutes to develop a noticeable discoloration and/or brittleness was noted.

Initial color was noted, as well as color at the time the noticeable discoloration had developed, and yellowness measured in a Hunter color difference meter, the difference in percent of yellowness being recorded.

The results are shown in Table VI.

TABLE VI

| Example No. | Phosphonite | Heat stability at 175° C. (minutes to failure) | % of Initial color |
|---|---|---|---|
| Control 1 | None | 70 | 25 |

TABLE VI-continued

| Example No. | Phosphonite | Heat stability at 175° C. (minutes to failure) | % of Initial color |
|---|---|---|---|
| Control 2 | [structure] | 90 | 20 |
| Control 3 | [structure] | 95 | 22 |
| Control 4 | [structure] | 90 | 19 |
| Example 40 | [structure] | 120 | 9 |

TABLE VI-continued
| Example No. | Phosphonite | Heat stability at 175° C. (minutes to failure) | % of Initial color |
|---|---|---|---|
| Example 41 | 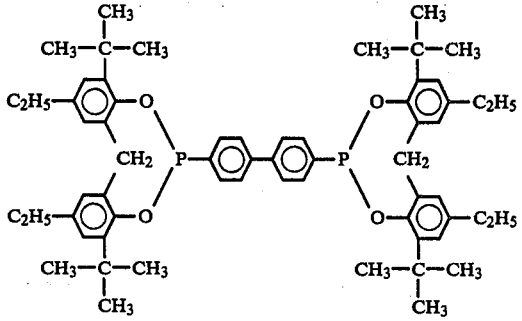 | 115 | 9 |
| Example 42 | 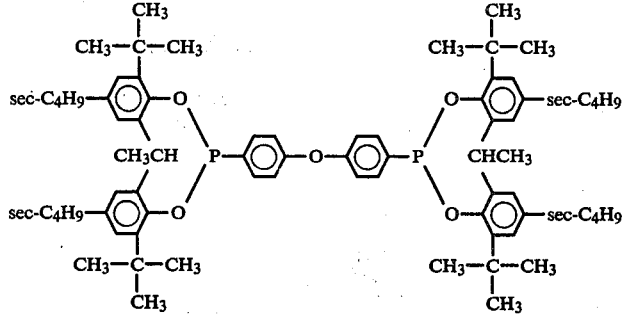 | 130 | 8 |
| Example 43 | 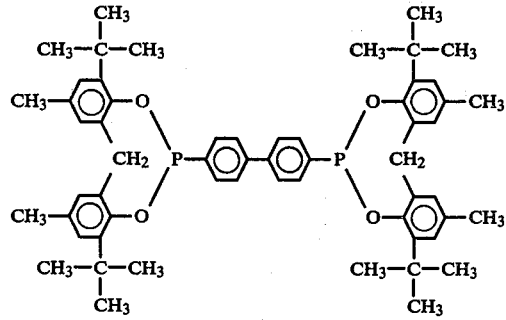 | 130 | 8 |
| Example 44 | 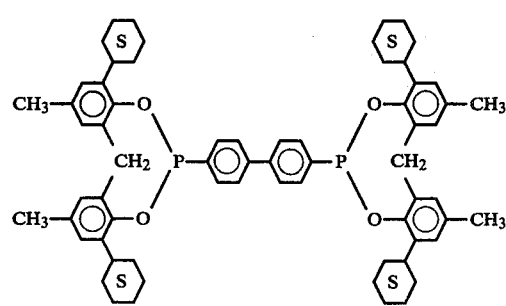 | 125 | 9 |

TABLE VI-continued

| Example No. | Phosphonite | Heat stability at 175° C. (minutes to failure) | % of Initial color |
|---|---|---|---|
| Example 45 | [structure: bis-phosphonite with biphenyl bridge, each P bearing two 2-methyl-4,6-di(1,1,3,3-tetramethylbutyl)phenoxy groups via CH2-O linkages] | 120 | 9 |

The superior effectiveness of the phosphonites of the invention, as compared to the Controls, in formulations otherwise the same, is apparent from the data.

EXAMPLES 46 TO 53

Polyester resin compositions were prepared using phosphonites of the invention and having the formulation:

| Ingredient | Parts by Weight |
|---|---|
| Polybutylene terephthalate | 100 |
| Pentaerythritol tetrakis(3,5-di-t-butyl-4-hydroxyphenyl)propionate | 0.2 |
| Phosphonite as shown in Table VII | 0.2 |

Compositions according to the above formulation were blended and injection-molded at 270° C. to prepare test pieces. Tensile strength of the pieces before and after heat ageing at 150° C. for 240 hours was determined, and the results are reported as the percent of tensile strength retained.

The results are shown in Table VII.

TABLE VII

| Example No. | Phosphonite | % Tensile strength Retained |
|---|---|---|
| Control 1 | None | 45 |
| Control 2 | [structure: bis-phosphonite with biphenyl bridge, each P bearing two 2,4-di-t-butyl-6-(1,1,3,3-tetramethylbutyl)phenoxy groups] | 64 |
| Control 3 | [structure: cyclic phosphonite with CH2 bridge, phenyl substituent on P, with di-t-butyl substituted phenoxy groups] | 67 |

TABLE VII-continued

| Example No. | Phosphonite | % Tensile strength Retained |
|---|---|---|
| Control 4 | (structure) | 69 |
| Example 46 | (structure) | 85 |
| Example 47 | (structure) | 91 |
| Example 48 | (structure) | 82 |

TABLE VII-continued
| Example No. | Phosphonite | % Tensile strength Retained |
|---|---|---|
| Example 49 | 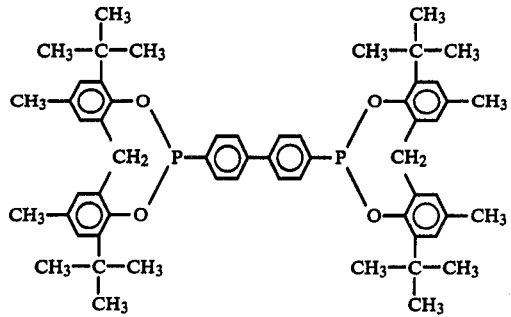 | 90 |
| Example 50 | 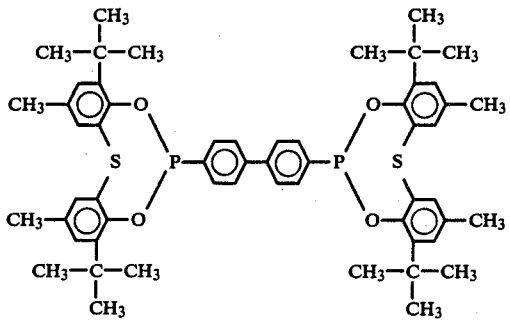 | 86 |
| Example 51 | 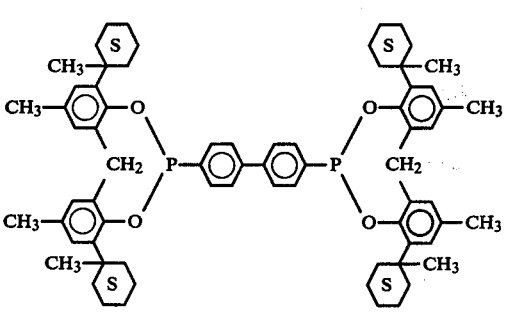 | 88 |
| Example 52 | 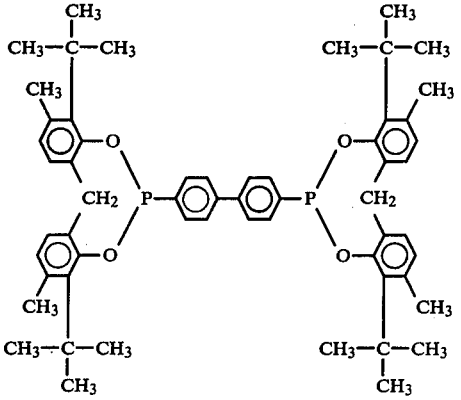 | 90 |

TABLE VII-continued

| Example No. | Phosphonite | % Tensile strength Retained |
|---|---|---|
| Example 53 | (bis-phosphonite with biphenylene bridge, each P bonded to two 2,4-di-t-C$_5$H$_{11}$-phenoxy groups linked via CH$_2$) | 88 |

The superior effectiveness of the phosphonites of the invention, as compared to the Controls, in formulations otherwise the same, is apparent from the data.

EXAMPLES 54 TO 58

Cis-1,4-polyisoprene polymer (M.W. 720,000) 100 g and the phosphonite shown in Table VIII 0.5 g were dissolved in 250 ml of isooctane, and then the isooctane was removed by evaporation.

The polyisoprene compositions were heated in a Geer oven at 100° C. for three hours, and the color of the compositions was observed. Their inherent viscosity (in toluene) was measured before and after heating.

The results are shown in Table VIII.

TABLE VIII

| Example No. | Phosphonite | Color | Inherent Viscosity Original | After heating |
|---|---|---|---|---|
| Control 1 | None | Brown | 3.6 | — |
| Control 2 | (bis-phosphonite with biphenylene bridge, each P bonded to two 2,4-di-t-butyl-phenoxy groups) | Pale brown | 4.5 | 3.9 |
| Control 3 | (same bis-phosphonite structure with di-t-butyl substituents) | Yellow | 4.7 | 4.1 |
| Control 4 | (phosphonite with phenyl and CH$_2$-bridged bis(di-t-butylphenoxy) group) | Pale brown | 4.6 | 3.9 |

TABLE VIII-continued

| Example No. | Phosphonite | Color | Inherent Viscosity Original | After heating |
|---|---|---|---|---|
| Example 54 | [structure] | Pale yellow | 4.9 | 4.6 |
| Example 55 | [structure] | Pale yellow | 4.9 | 4.6 |
| Example 56 | [structure] | Pale yellow | 4.9 | 4.7 |

TABLE VIII-continued

| Example No. | Phosphonite | Color | Inherent Viscosity Original | After heating |
|---|---|---|---|---|
| Example 57 | (structure shown) | Pale yellow | 4.9 | 4.5 |
| Example 58 | (structure shown) | Pale yellow | 4.9 | 4.6 |

The superior effectiveness of the phosphonites of the invention, as compared to the Controls, in formulations otherwise the same, is apparent from the data.

EXAMPLES 59 TO 65

Polycarbonate resin compositions were prepared having the following formulation:

| Ingredient | Parts by Weight |
|---|---|
| Polycarbonate | 100 |
| Phosphonite as shown in Table IX | 0.1 |

The ingredients were mixed and compression-molded at 260° C. to prepare sheets 1 mm thick. Heat stability was evaluated by heating the sheets in a Geer oven at 230° C. for thirty minutes, and then observing the color of the sheets.

The results are shown in Table IX.

TABLE IX

| Example No. | Phosphonite | Color of test piece |
|---|---|---|
| Control 1 | None | Dark brown |
| Control 2 | | Yellow |
| Control 3 | (structure shown) | Yellow |

TABLE IX-continued

| Example No. | Phosphonite | Color of test piece |
|---|---|---|
| Control 4 | (structure) | Yellow |
| Example 59 | (structure) | Pale yellow |
| Example 60 | (structure) | Pale yellow |

TABLE IX-continued
| Example No. | Phosphonite | Color of test piece |
|---|---|---|
| Example 61 | 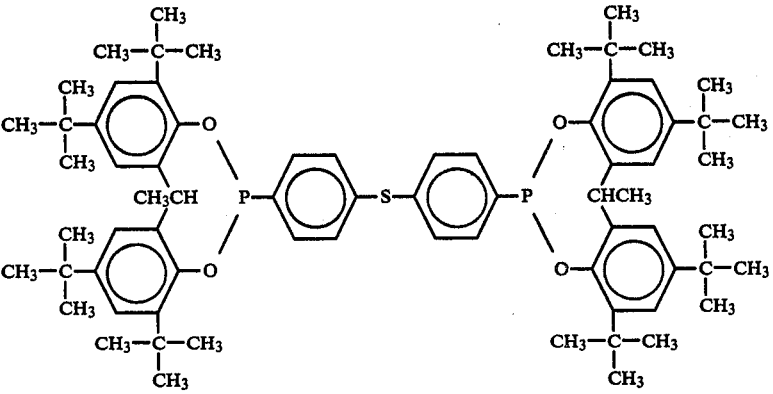 | Colorless |
| Example 62 | 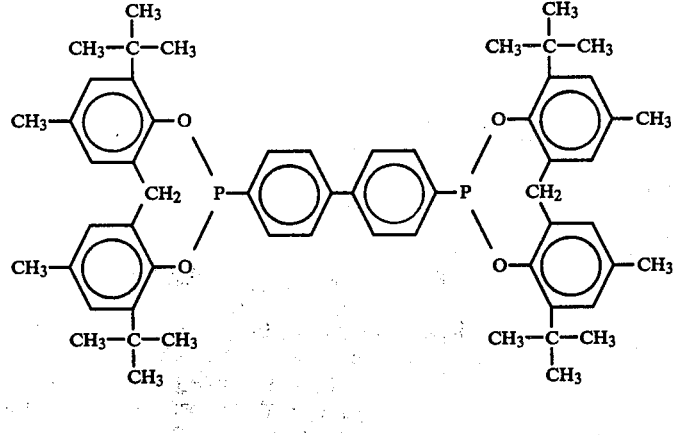 | Colorless |
| Example 63 | 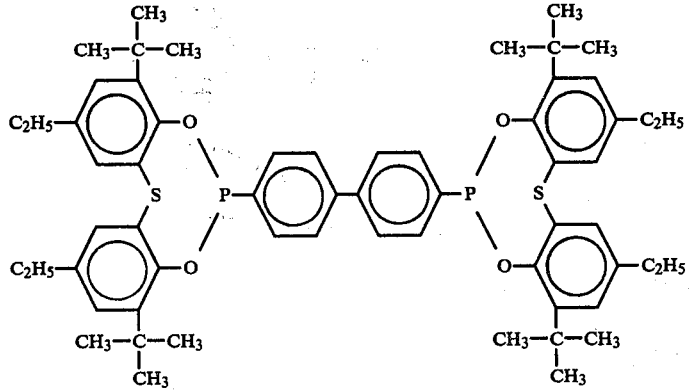 | Colorless |
| Example 64 | | Pale yellow |

TABLE IX-continued

| Example No. | Phosphonite | Color of test piece |
|---|---|---|
| Example 65 | 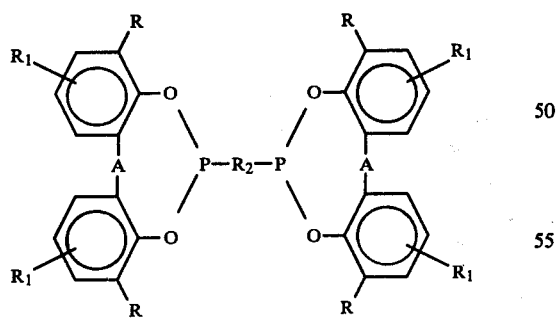 | Pale yellow |

The superior effectiveness of the phosphonites of the invention, as compared to the Controls, in formulations otherwise the same, is apparent from the data.

Having regard to the foregoing disclosure the following is claimed as the inventive and patentable embodiments thereof:

1. Hindered bisphenol diphosphonites having the structure:

[structure diagram with $R$, $R_1$, A, P, $R_2$ groups]

wherein:
A is selected from the group consisting of thio sulfur —S—; oxy oxygen —O—; alkylidene having from one to about ten carbon atoms; cycloalkylidene having from about four to about eight carbon atoms; and phenylalkylidene having from seven to about twelve carbon atoms;

R is selected from the group consisting of alkyl having from one to about eighteen carbon atoms; cycloalkyl having from three to about twelve carbon atoms; and aralkyl having from seven to about twelve carbon atoms;

$R_1$ is selected from the group consisting of hydrogen; alkyl having from one to about eighteen carbon atoms; cycloalkyl having from three to about twelve carbon atoms; and aralkyl having from seven to about twelve carbon atoms;

$R_2$ is selected from the group consisting of

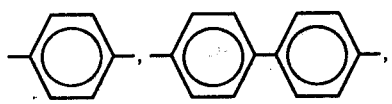

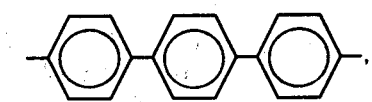

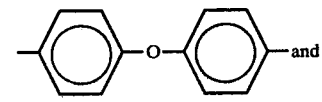 and

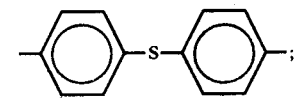

2. Hindered bisphenol diphosphonites according to claim 1 in which A is thio sulfur —S—.
3. Hindered bisphenol diphosphonites according to claim 1 in which A is oxy oxygen —O—.
4. Hindered bisphenol diphosphonites according to claim 1 in which A is alkylidene.
5. Hindered bisphenol diphosphonites according to claim 1 in which A is cycloalkylidene.
6. Hindered bisphenol diphosphonites according to claim 1 in which A is phenylalkylidene.
7. Hindered bisphenol diphosphonites according to claim 1 in which R is cycloalkyl.
8. Hindered bisphenol diphosphonites according to claim 1 in which R is alkyl.
9. Hindered bisphenol diphosphonites according to claim 1 in which $R_2$ is

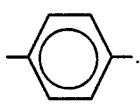

10. Hindered bisphenol diphosphonites according to claim 1 in which $R_2$ is

11. Hindered bisphenol diphosphonites according to claim 1 in which $R_2$ is

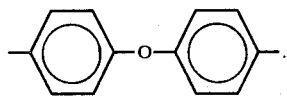

12. Hindered bisphenol diphosphonites according to claim 1 in which $R_2$ is

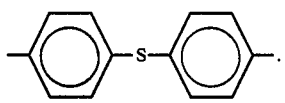

13. Hindered bisphenol diphosphonites according to claim 1 in which $R_2$ is

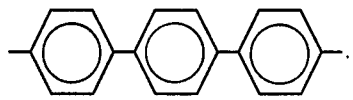

14. Hindered bisphenol diphosphonites according to claim 1 in which $R_1$ is hydrogen.
15. Hindered bisphenol diphosphonites according to claim 1 in which $R_1$ is alkyl.
16. Hindered bisphenol diphosphonites according to claim 1 in which $R_1$ is cycloalkyl.
17. Hindered bisphenol diphosphonites according to claim 1 in which $R_1$ is phenyl.
18. Hindered bisphenol diphosphonites according to claim 1 in which A is alkylidene, and $R_2$ is

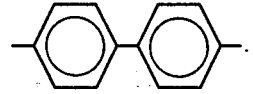

19. Hindered bisphenol diphosphonites according to claim 1 having the formula:

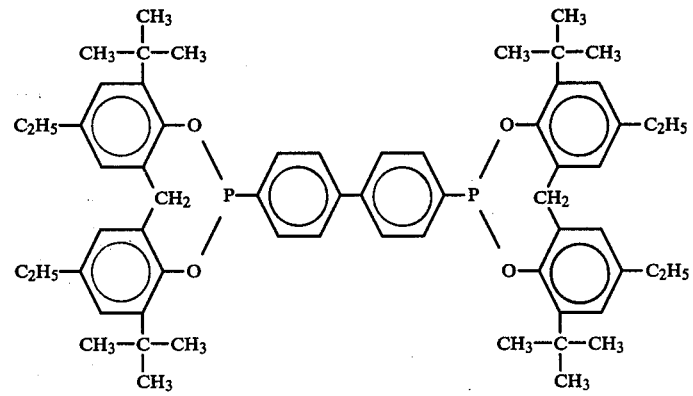

20. Hindered bisphenol diphosphonites according to claim 1 having the formula:

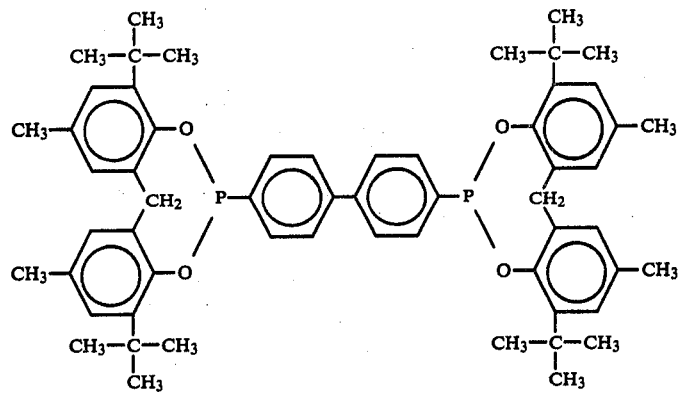
21. Hindered bisphenol diphosphonites according to claim 1 having the formula:
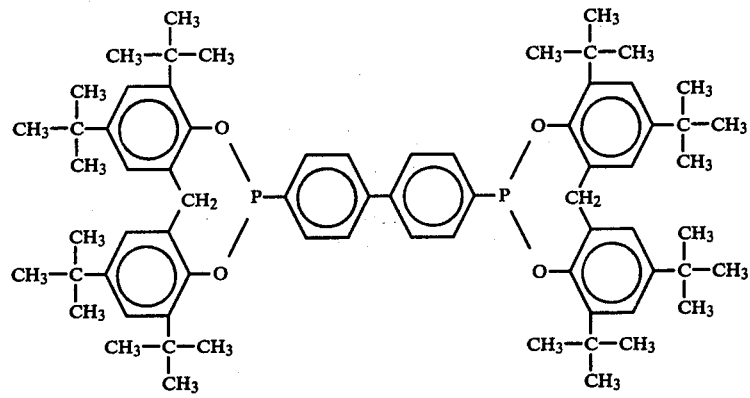
22. Hindered bisphenol diphosphonites according to claim 1 having the formula:
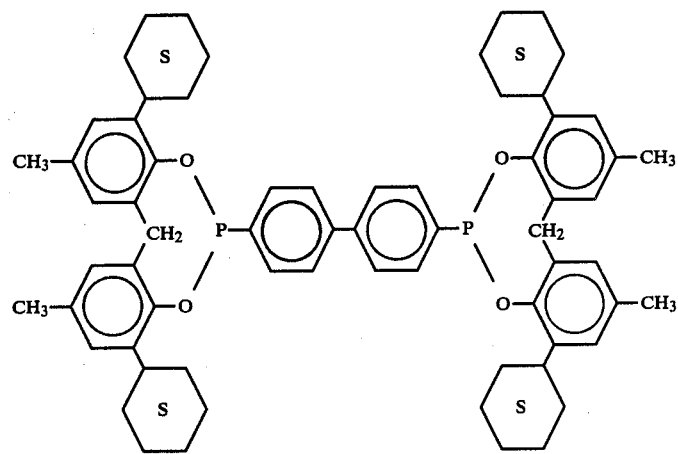
23. Hindered bisphenol diphosphonites according to claim 1 having the formula:

24. Hindered bisphenol diphosphonites according to claim 1 having the formula:

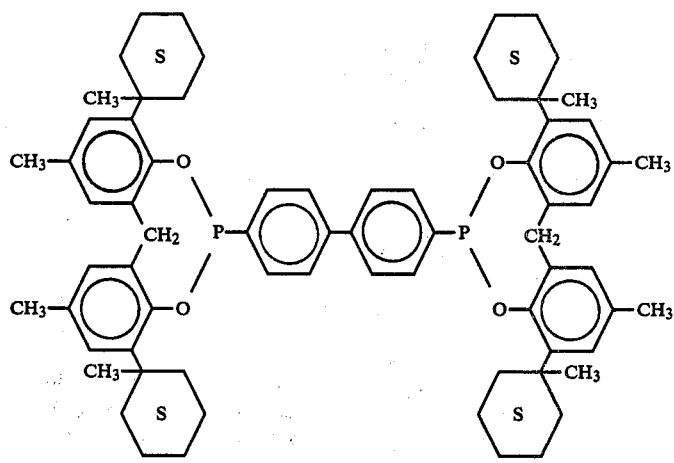

25. Hindered bisphenol diphosphonites according to claim 1 having the formula:

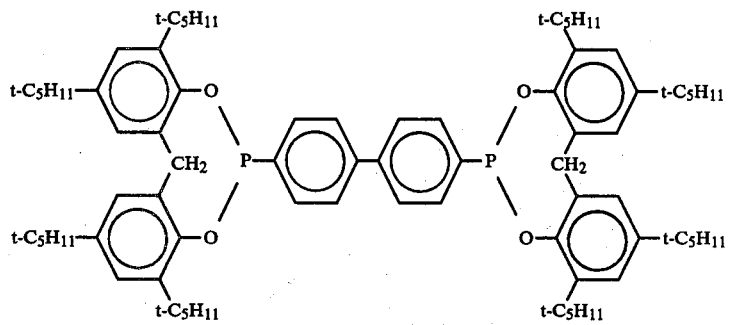

26. Hindered bisphenol diphosphonites according to claim 1 having the formula:

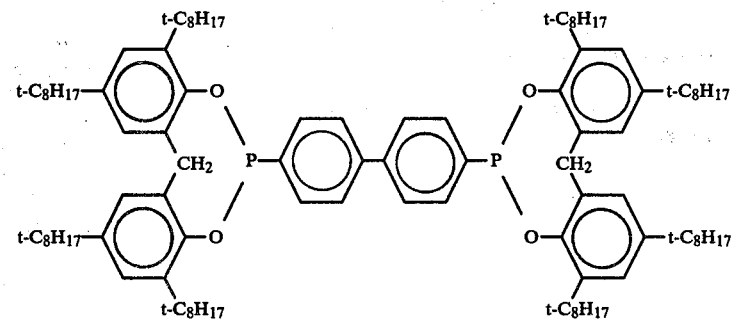

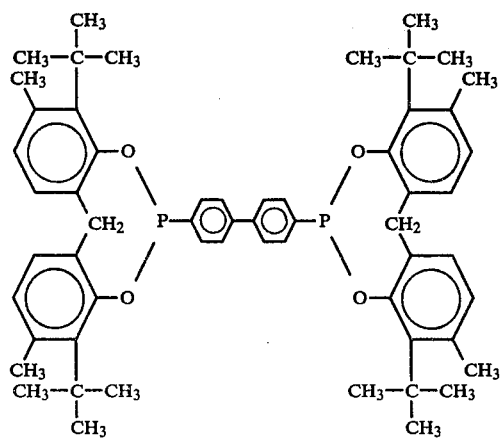

27. A polyvinyl chloride resin composition having improved resistance to deterioration when heat at 350° F., comprising a polyvinyl chloride resin formed at least in part of the recurring group:

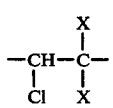

and having a chlorine content in excess of 40%, where X is either hydrogen or chlorine; and a compound in accordance with claim 1.

28. A polyvinyl chloride resin composition in accordance with claim 27 in which the polyvinyl chloride resin is polyvinyl chloride homopolymer.

29. A polyvinyl chloride resin composition in accordance with claim 27 in which the polyvinyl chloride resin is a copolmer of vinyl chloride and vinyl acetate.

30. An olefin polymer composition having improved resistance to deterioration comprising an olefin polymer selected from the group consisting of polymers of alpha-olefins having from two to six carbon atoms and polystyrene, and a compound in accordance with claim 1.

31. An olefin polymer composition in accordance with claim 30 wherein the polyolefin is polypropylene.

32. An olefin polymer composition in accordance with claim 30 wherein the polyolefin is polyethylene.

33. An olefin polymer composition in accordance with claim 30 wherein the polyolefin is cis-1,4-polyisoprene.

34. An acrylonitrile-butadiene-styrene polymer having its resistance to deterioration when heated at 300° F. and above enhanced by a compound in accordance with claim 1.

35. A polyester resin composition having improved resistance to deterioration comprising a polyester resin and a compound in accordance with claim 1.

36. An ethylene-vinyl acetate copolymer composition having improved resistance to deterioration comprising an ethylene-vinyl acetate copolymer and a compound in accordance with claim 1.

37. A polycarbonate composition having improved resistance to deterioration comprising a polyurethane and a compound in accordance with claim 1.

38. A polyphenylene oxide composition having improved resistance to deterioration comprising a polyphenylene oxide and a compound in accordance with claim 1.

* * * * *